(12) United States Patent
Hönel et al.

(10) Patent No.: US 8,771,903 B2
(45) Date of Patent: *Jul. 8, 2014

(54) METHOD FOR PRODUCING A HOLOGRAPHIC FILM

(75) Inventors: Dennis Hönel, Zülpich (DE);
Marc-Stephan Weiser, Leverkusen (DE); Friedrich-Karl Bruder, Krefeld (DE); Thomas Rölle, Leverkusen (DE); Thomas Fäcke, Leverkusen (DE)

(73) Assignee: Bayer MaterialScience AG (DE)

( * ) Notice: Subject to any disclaimer, the term of this patent is extended or adjusted under 35 U.S.C. 154(b) by 167 days.

This patent is subject to a terminal disclaimer.

(21) Appl. No.: 13/504,563

(22) PCT Filed: Nov. 2, 2010

(86) PCT No.: PCT/EP2010/066630
§ 371 (c)(1),
(2), (4) Date: Apr. 27, 2012

(87) PCT Pub. No.: WO2011/067057
PCT Pub. Date: Jun. 9, 2011

(65) Prior Publication Data
US 2012/0214089 A1    Aug. 23, 2012

(30) Foreign Application Priority Data

Nov. 3, 2009  (EP) .................................... 09013766

(51) Int. Cl.
*G03H 1/02*  (2006.01)
*G01N 5/04*  (2006.01)
*G03H 1/04*  (2006.01)

(52) U.S. Cl.
CPC ............. *G03H 1/04* (2013.01); *G03H 2227/04* (2013.01); *G03H 2260/12* (2013.01); *G03H 2260/54* (2013.01); *G01N 5/04* (2013.01)

USPC .................... 430/1; 430/2; 359/3; 374/14

(58) Field of Classification Search
None
See application file for complete search history.

(56) References Cited

U.S. PATENT DOCUMENTS 5,470,813 A    11/1995  Le-Khac
5,679,710 A *  10/1997  Davy et al. .................... 514/547

(Continued)

FOREIGN PATENT DOCUMENTS

EP    134861    *  3/1985
EP    0223587 A1    5/1987

(Continued)

OTHER PUBLICATIONS

International Search Report for PCT/EP2010/066630 mailed May 4, 2011.

*Primary Examiner* — Martin Angebranndt
(74) *Attorney, Agent, or Firm* — Drinker Biddle & Reath LLP

(57) ABSTRACT

The invention relates to a method for producing holographic films, in which a photopolymer formulation is provided which comprises as constituents matrix polymers, writing monomers, a photoinitiatior system, optionally a non-photopolymerizable component and optionally catalysts, radical stabilizers, solvents, additives and other auxiliaries and/or additives. The photopolymer formulation is applied in a planar manner and in the form of a film on a support film and the photopolymer formulation is dried on the support film at a temperature 60<T<120 DEG C, wherein only compounds are selected as components for the photopolymer formulation, the TGA 95 values of which are >100 DEG C and are above the temperature T by at least 30 DEG C, and a photopolymer formulation having a plateau module of =0.030 MPa is used.

15 Claims, 2 Drawing Sheets

(56) References Cited

U.S. PATENT DOCUMENTS

| | | |
|---|---|---|
| 7,008,900 B1 | 3/2006 | Hofmann et al. |
| 2003/0087104 A1* | 5/2003 | Dhar et al. ............... 428/422.8 |
| 2005/0185232 A1* | 8/2005 | Teranishi et al. ............. 359/3 |
| 2006/0166104 A1* | 7/2006 | Setthachayanon et al. ....... 430/1 |
| 2008/0254374 A1* | 10/2008 | Yamada et al. ............... 430/2 |
| 2008/0311483 A1* | 12/2008 | Stockel et al. ............... 430/2 |
| 2008/0312403 A1* | 12/2008 | Stockel et al. ............... 528/59 |
| 2009/0062419 A1* | 3/2009 | Stockel et al. .............. 522/109 |
| 2009/0087753 A1* | 4/2009 | Satou et al. ................. 430/2 |
| 2009/0185470 A1* | 7/2009 | Stoeckel et al. ............ 369/103 |
| 2010/0020373 A1* | 1/2010 | Askham .................... 359/3 |
| 2010/0036013 A1* | 2/2010 | Roelle et al. ............... 522/174 |
| 2010/0086860 A1* | 4/2010 | Roelle et al. ................ 430/2 |
| 2010/0086861 A1* | 4/2010 | Weiser et al. ................ 430/2 |
| 2010/0087564 A1* | 4/2010 | Weiser et al. ............... 522/95 |
| 2010/0112459 A1* | 5/2010 | Weiser et al. ................ 430/2 |
| 2010/0203241 A1* | 8/2010 | Weiser et al. .............. 427/162 |
| 2011/0065827 A1* | 3/2011 | Facke et al. ............... 522/173 |
| 2011/0189591 A1* | 8/2011 | Weiser et al. ................ 430/2 |
| 2011/0236803 A1* | 9/2011 | Weiser et al. ................ 430/2 |
| 2011/0311905 A1* | 12/2011 | Honel et al. ................. 430/2 |
| 2012/0214090 A1* | 8/2012 | Weiser et al. ................ 430/2 |
| 2012/0214895 A1* | 8/2012 | Rolle et al. ................ 522/78 |
| 2012/0219883 A1* | 8/2012 | Bruder et al. ................ 430/2 |
| 2012/0219884 A1* | 8/2012 | Weiser et al. ................ 430/2 |
| 2012/0219885 A1* | 8/2012 | Facke et al. ................. 430/2 |
| 2012/0231376 A1* | 9/2012 | Rolle et al. .................. 430/2 |
| 2012/0231377 A1* | 9/2012 | Weiser et al. ................ 430/2 |
| 2012/0237856 A1* | 9/2012 | Rolle et al. .................. 430/2 |
| 2012/0302659 A1* | 11/2012 | Rolle et al. ................. 522/173 |
| 2012/0321997 A1* | 12/2012 | Rolle et al. .................. 430/2 |
| 2012/0321998 A1* | 12/2012 | Rolle et al. .................. 430/2 |
| 2013/0177746 A1* | 7/2013 | Facke et al. ............... 428/195.1 |
| 2013/0224634 A1* | 8/2013 | Berneth et al. .............. 430/2 |
| 2013/0252140 A1* | 9/2013 | Facke et al. ................. 430/2 |

FOREIGN PATENT DOCUMENTS

| | | |
|---|---|---|
| EP | 684222 * | 11/1995 |
| EP | 0700949 A2 | 3/1996 |
| EP | 0743093 A1 | 11/1996 |
| EP | 0761708 A2 | 3/1997 |
| EP | 2154129 A1 | 2/2010 |
| EP | 2396358 A1 | 12/2011 |
| WO | WO-97/40086 A1 | 10/1997 |
| WO | WO-98/16310 A1 | 4/1998 |
| WO | WO-00/47649 A1 | 8/2000 |
| WO | WO-03/014178 A1 | 2/2003 |
| WO | WO-2008/125199 A1 | 10/2008 |

* cited by examiner

METHOD FOR PRODUCING A HOLOGRAPHIC FILM

CROSS-REFERENCE TO RELATED APPLICATIONS

This application is a national stage application (under 35 U.S.C. §371) of PCT/EP2010/066630, filed Nov. 2, 2010, which claims benefit of European application 09013766.2, filed Nov. 3, 2009, both of which are incorporated herein by reference in their entirety for all their useful purposes.

BACKGROUND

The invention relates to a process for producing a holographic film and to a holographic film obtainable by the process.

Holographic films can be produced, for example, with the aid of special photopolymer formulations. Thus, for example, WO 2008/125199 A1 describes a photopolymer formulation which contains polyurethane-based matrix polymers, an acrylate-based writing monomer and photoinitiators. If a layer of the photopolymer formulation is cured, the writing monomer and the photoinitiators are embedded with an isotropic distribution in space in the resulting polyurethane matrix. In this way, a film into which holograms can be incorporated by exposure to light is obtained.

This can be effected by means of the superposition of two coherent light sources, a three-dimensional structure which in general can be described by a regional change in the refractive index (refractive index modulation $\Delta n$) forming in the medium. Such structures are referred to as holograms, which can also be described as diffractive optical elements. The optical functions which are performed by such a hologram depend on the specific exposure to light.

For the uses of photopolymer formulations, the refractive index modulation $\Delta n$ produced by the holographic exposure to light in the photopolymer plays the decisive role. During the holographic exposure to light, the interference field of signal and reference light beam (in the simplest case, that of two plane waves is formed by the local photopolymerization of, for example, highly refractive acrylates at sites of high intensity in the interference field in a refractive index grating. The refractive index grating in the photopolymer (the hologram) contains all information of the signal light beam. By exposing the hologram only to the reference light beam, the signal can then be reconstructed. The strength of the signal reconstructed in this manner in relation to the strength of the incident reference light is referred to as diffraction efficiency or DE below. In the simplest case of a hologram which forms from the superposition of two plane waves, the DE is obtained from the quotient of the intensity of the light diffracted in the reconstruction and the sum of the intensities of incident reference light and diffracted light. The higher the DE, the more efficient is a hologram with respect to the quantity of reference light which is required in order to make the signal visible with a fixed brightness.

Highly refractive acrylates are capable of producing refractive index gratings having a high amplitude between regions with low refractive index and regions with high refractive index and hence permitting holograms with high DE and high $\Delta n$ in photopolymer formulations. It should be noted that DE is dependent on the product of $\Delta n$ and the photopolymer layer thickness d. The greater the product, the greater the possible DE (for reflection holograms). The width of the angular range in which the hologram becomes visible (reconstructed), for example in the case of exposure to monochromatic light, depends only on the layer thickness d. In the case of exposure of the hologram to, for example, white light, the width of the spectral region which can contribute to the reconstruction of the hologram likewise depends only on the layer thickness d. The smaller d, the greater are the respective acceptance widths.

If it is intended to produce bright and readily visible holograms, a high $\Delta n$ and small thickness d should be strived for, in particular so that DE is as large as possible. This means that the higher $\Delta n$, the more latitude achieved for establishing the layer thickness d for bright holograms without loss of DE. The optimization of $\Delta n$ in the optimization of photopolymer formulations is therefore of outstanding importance (P. Hariharan, Optical Holography, 2nd Edition, Cambridge University Press, 1996).

Attempts have therefore been made to date to realize as high a $\Delta n$ as possible by changing the composition of the photopolymer formulations used for the production of the holographic films. However, it has been found that the photopolymer formulations developed in laboratory experiments cannot be used without considerable problems in some cases for the industrial production of holographic films.

Such an industrial production process is described, for example, in European Patent Application not laid open as yet and having the application number 09001952.2. In this process, a photopolymer formulation is applied to a substrate material and then dried at elevated temperature. In this way, holographic media in the form of films can be obtained.

If the photopolymer formulations optimized in laboratory experiments for a high $\Delta n$ are used in the process described above, on the one hand films which do not have sufficient mechanical stability are obtained in many cases, so that crushing of the applied photopolymer formulation occurs during winding onto a roll. This is particularly disadvantageous since the films cannot be wound up as rolls without destruction.

On the other hand, it is true that it is possible to use films which have sufficient mechanical stability. However, holograms which were written into these films do not have the desired high $\Delta n$ values.

It has therefore not been directly possible to date to produce holographic films on the industrial scale which both have the necessary mechanical stability and strength and are suitable for writing of holograms having high $\Delta n$ values.

BRIEF DESCRIPTION OF EMBODIMENTS

It was therefore an object of the present invention to provide a (industrial) process with the aid of which it is possible to produce holographic films which both have the necessary mechanical stability and strength and are suitable for writing of holograms having high $\Delta n$ values.

This object is achieved by a process for producing a holographic film in which
  i) a photopolymer formulation comprising, as components,
     A) matrix polymers
     B) writing monomers
     C) photoinitiator system
     D) optionally a non-photopolymerizable component
     E) and optionally catalysts, free radical stabilizers, solvents, additives and other auxiliaries and/or additives
     is provided,
  ii) the photopolymer formulation is applied extensively as a film to a substrate and
  iii) the photopolymer formulation is dried on the substrate at a temperature of 60<T<120° C., components chosen for the photopolymer formulation being only compounds whose TGA 95 values are >100° C. and are at least 30° C. above the temperature T and a photopolymer formulation having a plateau modulus of ≥30 000 Pa being used.

BRIEF DESCRIPTION OF THE DRAWINGS

The foregoing brief description, as well as the following detailed description, may be better understood when read in conjunction with the appended drawings. For the purpose of assisting in the explanation of the invention, there are shown in the drawings representative embodiments which are considered illustrative. It should be understood, however, that the invention is not limited in any manner to the precise arrangements and instrumentalities shown.

In the drawings.

DETAILED DESCRIPTION OF EMBODIMENTS

Figure 1:
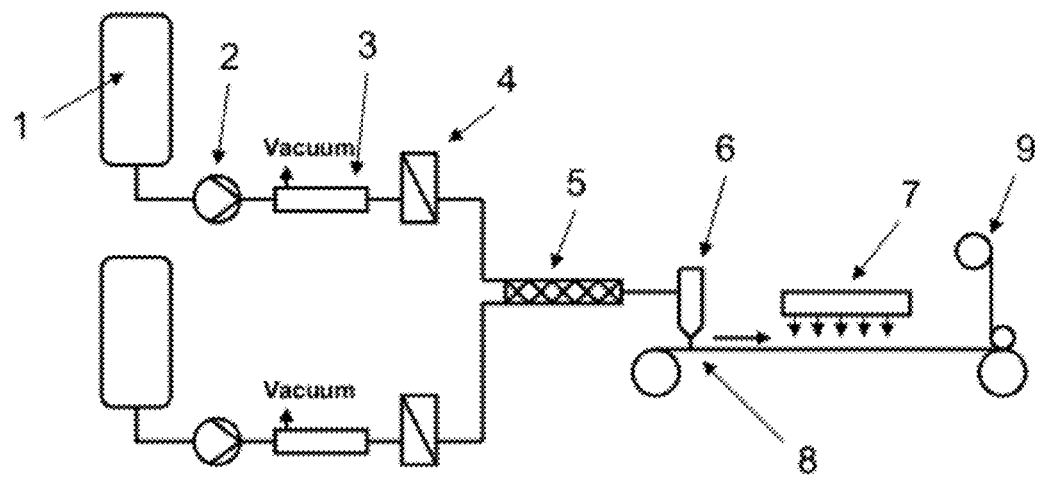
FIG. 1 illustrates a schematic setup of a typical coating unit.

In the context of the present application, plateau modulus is understood as meaning the real part of the complex shear modulus (also referred to as storage modulus) of the unexposed photopolymer formulation.

The plateau modulus of the photopolymer formulation can be determined in particular by measuring the complex shear modulus of the photopolymer formulation in an oscillation rheometer with plate-plate geometry. Particularly if the matrix component A consists of reactive components (e.g. a 2-component system), the trend in the shear modulus of the photopolymer formulation as a function of time over the curing time of the matrix component can be monitored thereby, at the end of which the plateau modulus occurs as the real part of the resulting complex shear modulus. In order to enable the measurement of the plateau modulus to be carried out more easily, the photoinitiator system (component C)) in the photopolymer formulation can be dispensed with.

Preferably, the photopolymer formulation can be dried at a temperature of 70<T<100° C.

The TGA 95 values of the individual components can be determined in particular by weighing an amount of about 10 mg of the sample of the respective component into a small aluminium pan having a volume of 70 μl, introducing the small aluminium pan an oven of a thermobalance, preferably a TG50 thermobalance from Mettler-Toledo, and measuring the loss of mass of the sample in the open small aluminium pan at a constant oven heating rate of 20 K/min, the start temperature of the oven being 30° C. and the end temperature 600° C., the oven being flushed with a 200 ml/min nitrogen stream during the determination and the temperature at which a loss of mass of the sample of 5% by weight, based on the originally weighed in amount of the sample, has occurred being determined as the TGA 95 value of the respective component.

Preferably, a photopolymer formulation having a plateau modulus of ≥0.03 MPa and ≤1 MPa, preferably of ≥0.05 MPa and ≤1 MPa, particularly preferably of ≥0.1 MPa and ≤1 MPa and especially preferably of ≥0.1 MPa and ≤0.6 MPa can be used.

According to a further preferred embodiment of the invention, it is intended to apply a laminating film to the film after the drying in step iii). The film can then preferably be rolled up together with the laminating film.

The matrix polymers can preferably be polyurethanes, which are obtainable in particular by reacting an isocyanate component a) with an isocyanate-reactive component b).

Furthermore, photopolymer formulations comprising matrix polymers obtainable by reacting a polyisocyanate component a) with an isocyanate-reactive component b), at least two different compounds which have groups reacting under the action of actinic radiation with ethylenically unsaturated compounds with polymerization (radiation-curing groups) and are themselves free of NCO groups are preferred as writing monomers B), photoinitiators C), free radical stabilizers E), optionally catalysts E) and optionally auxiliaries and additives E).

The isocyanate component a) preferably comprises polyisocyanates. Polyisocyanates which may be used are all compounds known per se to a person skilled in the art or mixtures thereof, which have on average two or more NCO functions per molecule. These may have an aromatic, araliphatic, aliphatic or cycloaliphatic basis. Monoisocyanates and/or polyisocyanates containing unsaturated groups may also be concomitantly used in minor amounts.

For example, butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate, the isomeric bis(4,4'-isocyanatocyclohexyl)methane and mixtures thereof having any desired isomer content, isocyanatomethyl-1,8-octane diisocyanate, 1,4-cyclohexylene diisocyanate, the isomeric cyclohexanedimethylene diisocyanates, 1,4-phenylene diisocyanate, 2,4- and/or 2,6-toluene diisocyanate, 1,5-naphthylene diisocyanate, 2,4'- or 4,4'-diphenylmethane diisocyanate and/or triphenylmethane 4,4',4"-triisocyanate are suitable.

Use of derivatives of monomeric di- or triisocyanates having urethane, urea, carbodiimide, acylurea, isocyanurate, allophanate, biuret, oxadiazinetrione, uretdione and/or iminooxadi-azinedione structures is also possible.

The use of polyisocyanates based on aliphatic and/or cycloaliphatic di- or triisocyanates is preferred.

Particularly preferably, the polyisocyanates of component a) are di- or oligomerized aliphatic and/or cycloaliphatic di- or triisocyanates.

Isocyanurates, uretdiones and/or iminooxadiazinediones based on HDI and 1,8-diisocyanato-4-(isocyanatomethyl)octane or mixtures thereof are very particularly preferred.

Likewise, NCO-functional prepolymers having urethane, allophanate, biuret and/or amide groups can be used as component a). Prepolymers of component a) are obtained in a manner well known per se to the person skilled in the art by reacting monomeric, oligomeric or polyisocyanates a1) with isocyanate-reactive compounds a2) in suitable stoichiometry with optional use of catalysts and solvents.

Suitable polyisocyanates a1) are all aliphatic, cycloaliphatic, aromatic or araliphatic di- and triisocyanates known per se to the person skilled in the art, it being unimportant whether these were obtained by means of phosgenation or by phosgene-free processes. In addition, the higher molecular weight subsequent products of monomeric di- and/or triisocyanates having a urethane, urea, carbodiimide, acylurea, isocyanurate, allophanate, biuret, oxadiazinetrione, uretdione or iminooxadiazinedione structure, which are well known per se to a person skilled in the art, can also be used, in each case individually or in any desired mixtures with one another.

Examples of suitable monomeric di- or triisocyanates which can be used as component a1) are butylene diisocyanate, hexamethylene diisocyanate (HDI), isophorone diisocyanate (IPDI), trimethylhexamethylene diisocyanate (TMDI), 1,8-diisocyanato-4-(isocyanatomethyl)octane, isocyanatomethyl-1,8-octane diisocyanate (TIN), 2,4- and/or 2,6-toluene diisocyanate.

OH-functional compounds are preferably used as isocyanate-reactive compounds a2) for synthesizing the prepolymers. Said compounds are analogous to the OH-functional compounds as described below for the component b).

Preferred OH-functional compounds in a2) are polyester polyols and/or polyether polyols having number average molar masses of 200 to 6200 g/mol. Difunctional polyether polyols based on ethylene glycol and propylene glycol, the proportion of propylene glycol accounting for at least 40% by weight, and polymers of tetrahydrofuran having number average molar masses of 200 to 4100 g/mol and aliphatic polyester polyols having number average molar masses of 200 to 3100 g/mol are particularly preferred.

Difunctional polyether polyols based on ethylene glycol and propylene glycol, the proportion of propylene glycol accounting for at least 80% by weight (in particular pure polypropylene glycols), and polymers of tetrahydrofuran having number average molar masses of 200 to 2100 g/mol are very particularly preferred. Adducts of butyrolactone, ε-caprolactone and/or methyl-ε-caprolactone (in particular ε-caprolactone) with aliphatic, araliphatic or cycloaliphatic di-, tri- or polyfunctional alcohols containing 2 to 20 carbon atoms (in particular difunctional aliphatic alcohols having 3 to 12 carbon atoms) are likewise very particularly preferred. These adducts preferably have number average molar masses of 200 to 2000 g/mol, particularly preferably of 500 to 1400 g/mol.

Allophanates may also be used as a mixture with other prepolymers or oligomers of component a1). In these cases, the use of OH-functional compounds having functionalities of 1 to 3.1 is advantageous. When monofunctional alcohols are used, those having 3 to 20 carbon atoms are preferred.

It is also possible to use amines for the prepolymer preparation. For example, ethylenediamine, diethylenetriamine, triethylenetetramine, propylenediamine, diaminocyclohexane, diaminobenzene, diaminobisphenyl, difunctional polyamines, for example, the Jeffamines®, amine-terminated polymers having number average molar masses of up to 10 000 g/mol or any desired mixtures thereof with one another are suitable.

For the preparation of prepolymers containing biuret groups, an excess of isocyanate is reacted with amine, a biuret group forming. In this case, suitable amines for the reaction with the di-, tri- and polyisocyanates mentioned are all oligomeric or polymeric, primary or secondary, difunctional amines of the abovementioned type. Aliphatic biurets based on aliphatic amines and aliphatic isocyanates are preferred. Low molecular weight biurets having number average molar masses of less than 2000 g/mol, based on aliphatic diamines or difunctional polyamines and aliphatic diisocyanates, in particular HDI and TMDI, are particularly preferred.

Preferred prepolymers are urethanes, allophanates or biurets obtained from aliphatic isocyanate-functional compounds and oligomeric or polymeric isocyanate-reactive compounds having number average molar masses of 200 to 10 000 g/mol; urethanes, allophanates or biurets obtained from aliphatic isocyanate-functional compounds and polyols having number average molar masses of 200 to 6200 g/mol or (poly)amines having number average molar masses of less than 3000 g/mol are particularly preferred and allophanates obtained from HDI or TMDI and difunctional polyether polyols (in particular polypropylene glycols) having number average molar masses of 200 to 2100 g/mol, urethanes obtained from HDI or TMDI, based on adducts of butyrolactone, ε-caprolactone and/or methyl-ε-caprolactone (in particular ε-caprolactone) with aliphatic, araliphatic or cycloaliphatic di-, tri- or polyfunctional alcohols containing 2 to 20 carbon atoms (in particular with difunctional aliphatic alcohols having 3 to 12 carbon atoms), having number average molar masses of 500 to 3000 g/mol, particularly preferably of 1000 to 2000 g/mol (in particular as a mixture with other oligomers of difunctional aliphatic isocyanates) or urethanes obtained from HDI or TMDI, based on trifunctional polyether polyols (in particular polypropylene glycol) having number average molar masses between 2000 and 6200 g/mol and biurets obtained from HDI or TMDI with difunctional amines or polyamines having number average molar masses of 200 to 1400 g/mol (in particular also as a mixture with other oligomers of difunctional aliphatic isocyanates) are very particularly preferred.

The prepolymers described above preferably have residue contents of free monomeric isocyanate of less than 2% by weight, particularly preferably less than 1.0% by weight, very particularly preferably less than 0.5% by weight.

Of course, the isocyanate component may contain proportionately further isocyanate components in addition to the prepolymers described. Aromatic, araliphatic, aliphatic and cycloaliphatic di-, tri- or polyisocyanates are suitable for this purpose used. It is also possible to use mixtures of such di-, tri- or polyisocyanates. Examples of suitable di-, tri- or polyisocyanates are butylene diisocyanate, hexamethylene diisocyanate (HDI), isophorone diisocyanate (IPDI), 1,8-diisocyanato-4-(isocyanatomethyl)octane, 2,2,4- and/or 2,4,4-trimethylhexamethylene diisocyanate (TMDI), the isomeric bis(4,4'-isocyanatocyclo-hexyl)methanes and mixtures thereof having any desired isomer content, isocyanatomethyl-1,8-octane diisocyanate, 1,4-cyclohexylene diisocyanate, the isomeric cyclohexanedi-methylene diisocyanates, 1,4-phenylene diisocyanate, 2,4- and/or 2,6-toluene diisocyanate, 1,5-naphthylene diisocyanate, 2,4'- or 4,4'-diphenylmethane diisocyanate, triphenylmethane 4,4',4''-triisocyanate or derivatives thereof having a urethane, urea, carbodiimide, acylurea, isocyanurate, allophanate, biuret, oxadiazinetrione, uretdione, or iminooxadiazinedione structure and mixtures thereof. Polyisocyanates based on oligomerized and/or derivatized diisocyanates which were freed from excess diisocyanate by suitable processes are preferred, in particular those of hexamethylene diisocyanate. The oligomeric isocyanurates, uretdiones and iminooxadiazinediones of HDI and mixtures thereof are particularly preferred.

It is optionally also possible for the isocyanate component a) proportionately to contain isocyanates which have been partly reacted with isocyanate-reactive ethylenically unsaturated compounds. α,β-Unsaturated carboxylic acid derivatives, such as acrylates, methacrylates, maleates, fumarates, maleimides, acrylamides and vinyl ethers, propenyl ethers, allyl ethers and compounds which contain dicyclopentadienyl units and have at least one group reactive towards isocyanates are preferably used here as isocyanate-reactive ethylenically unsaturated compounds; these are particularly preferably acrylates and methacrylates having at least one isocyanate-reactive group. Suitable hydroxy-functional acrylates or methacrylates are, for example, compounds such as 2-hydroxyethyl (meth)acrylate, polyethylene oxide mono (meth)acrylates, polypropylene oxide mono(meth)-acrylates, polyalkylene oxide mono(meth)acrylates, poly(ε-caprolactone) mono(meth)-acrylates, such as, for example, Tone® M100 (Dow, USA), 2-hydroxypropyl (meth)acrylate, 4-hydroxybutyl (meth)acrylate, 3-hydroxy-2,2-dimethylpropyl (meth)acrylate, the hydroxy-functional mono-, di- or tetra (meth)acrylates of polyhydric alcohols, such as trimethylolpropane, glycerol, pentaerythritol, dipentaerythritol, ethoxylated, propoxylated or alkoxylated trimethylolpropane, glycerol, pentaerythritol, dipentaerythritol or the industrial mixtures thereof. In addition, isocyanate-reactive oligomeric or polymeric unsaturated compounds containing acrylate and/or methacrylate groups, alone or in combination with the abovementioned monomeric compounds, are suitable. The proportion of isocyanates which have been partly reacted with isocyanate-reactive ethylenically unsaturated compounds, based on the isocyanate component a), is 0 to 99%, preferably 0 to 50%, particularly preferably 0 to 25% and very particularly preferably 0 to 15%.

It is optionally also possible for the abovementioned isocyanate component a) to contain, completely or proportionately, isocyanates which have been reacted completely or partly with blocking agents known to the person skilled in the art from coating technology. The following may be mentioned as an example of blocking agents: alcohols, lactams, oximes, malonic esters, alkyl acetoacetates, triazoles, phenols, imidazoles, pyrazoles and amines, such as, for example, butanone oxime, diisopropylamine, 1,2,4-triazole, dimethyl-1,2,4-triazole, imidazole, diethyl malonate, ethyl acetoacetate, acetone oxime, 3,5-dimethylpyrazole, ε-caprolactam, N-tert-butylbenzylamine, cyclopentanone carboxyethyl ester or any desired mixtures of these blocking agents.

In principle, all polyfunctional, isocyanate-reactive compounds which have on average at least 1.5 isocyanate-reactive groups per molecule can be used as component b).

Isocyanate-reactive groups in the context of the present invention are preferably hydroxy, amino or thio groups; hydroxy compounds are particularly preferred.

Suitable polyfunctional, isocyanate-reactive compounds are, for example, polyester, polyether, polycarbonate, poly(meth)acrylate and/or polyurethane polyols.

In addition, aliphatic, araliphatic or cycloaliphatic di-, tri- or polyfunctional alcohols having low molecular weights, i.e. having molecular weights of less than 500 g/mol, and short chains, i.e. containing 2 to 20 carbon atoms, are also suitable as polyfunctional, isocyanate-reactive compounds as constituents of component b).

These may be, for example, ethylene glycol, diethylene glycol, triethylene glycol, tetraethylene glycol, dipropylene glycol, tripropylene glycol, 1,2-propanediol, 1,3-propanediol, 1,4-butanediol, neopentyl glycol, 2-ethyl-2-butyl-propanediol, trimethylpentanediol, positional isomers of diethyloctanediol, 1,3-butylene glycol, cyclohexanediol, 1,4-cyclohexanedimethanol, 1,6-hexanediol, 1,2- and 1,4-cyclohexanediol, hydrogenated bisphenol A (2,2-bis(4-hydroxycyclohexyl)propane), 2,2-dimethyl-3-hydroxy-propionic acid (2,2-dimethyl-3-hydroxypropyl ester). Examples of suitable triols are trimethylolethane, trimethylolpropane or glycerol. Suitable higher-functional alcohols are ditrimethylolpropane, pentaerythritol, dipentaerythritol or sorbitol.

Suitable polyester polyols are, for example, linear polyester diols or branched polyester polyols, as are obtained in a known manner from aliphatic, cycloaliphatic or aromatic di- or polycarboxylic acids or their anhydrides with polyhydric alcohols having an OH functionality of ≥2.

Examples of such di- or polycarboxylic acids or anhydrides are succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid and acid anhydrides such as o-phthalic, trimellitic or succinic anhydride or any desired mixtures thereof with one another.

Examples of such suitable alcohols are ethanediol, di-, tri- and tetraethylene glycol, 1,2-propanediol, di-, tri- and tetrapropylene glycol, 1,3-propanediol, butanediol-1,4, butanediol-1,3, butanediol-2,3, pentanediol-1,5, hexanediol-1,6,2, 2-dimethyl-1,3-propanediol, 1,4-di-hydroxycyclohexane, 1,4-dimethylolcyclohexane, 1,8-octanediol, 1,10-decanediol, 1,12-dodecanediol, trimethylolpropane, glycerol or any desired mixtures thereof with one another.

Preferred polyester polyols are based on aliphatic alcohols and mixtures of aliphatic and aromatic acids and have number average molar masses between 500 and 10 000 g/mol and functionalities between 1.8 and 6.1.

Particularly preferred polyester polyols are based on aliphatic diols, such as butane-1,4-diol, hexane-1,6-diol, neopentyl glycol, ethanediol, propylene glycol, 1,3-butylene glycol, di-, tri-, or polyethylene glycol, di-, tri- and/or tetrapropylene glycol or mixtures of the abovementioned diols with aliphatic higher-functional alcohols, such as trimethylolpropane and/or pentaerythritol, the proportion of the higher-functional alcohols preferably accounting for less than 50% by weight (particularly preferably less than 30% by weight), based on the total amount of the alcohol used, in combination with aliphatic di- or polycarboxylic acids or anhydrides such as adipic acid and/or succinic acid, or mixtures of the above-mentioned aliphatic polycarboxylic acids or anhydrides with aromatic polycarboxylic acids or anhydrides, such as terephthalic acid and/or isophthalic acid, the proportion of the aromatic polycarboxylic acids or anhydrides preferably accounting for less than 50% by weight (and particularly preferably less than 30% by weight), based on the total amount of the polycarboxylic acids or anhydrides used. Particularly preferred polyester polyols have number average molar masses between 1000 and 6000 g/mol and functionalities between 1.9 and 3.3.

The polyester polyols may also be based on natural raw materials, such as castor oil. It is also possible for the polyester polyols to be based on homo- or copolymers of lactones, as can preferably be obtained by an addition reaction of lactones or lactone mixtures in a ring-opening lactone polymerization, such as butyrolactone, ε-caprolactone and/or methyl-ε-caprolactone, with hydroxy-functional compounds, such as polyhydric alcohols having an OH functionality of ≥2 or polyols having a functionality of greater than 1.8, for example of the abovementioned type.

Preferred polyols which are used as starters here are polyether polyols having a functionality of 1.8 to 3.1 and number average molar masses of 200 to 4000 g/mol; poly(tetrahydrofurans) having a functionality of 1.9 to 2.2 and number average molar masses of 500 to 2000 g/mol (in particular 600 to 1400 g/mol) are particularly preferred. As adducts are butyrolactone, E-caprolactone and/or methyl-ε-caprolactone, ε-caprolactone is particularly preferred.

Such polyester polyols preferably have number average molar masses of 400 to 6000 g/mol, particularly preferably of 800 to 3000 g/mol. Their OH functionality is preferably 1.8 to 3.5, particularly preferably 1.9 to 2.2.

Suitable polycarbonate polyols are obtainable in a manner known per se by reaction of organic carbonates or phosgene with diols or diol mixtures.

Suitable organic carbonates are dimethyl, diethyl and diphenyl carbonate.

Suitable diols or mixtures comprise the polyhydric alcohols mentioned in the context of the polyester segments and having an OH functionality of ≥2, preferably 1,4-butanediol, 1,6-hexanediol and/or 3-methylpentanediol, or polyester polyols can be converted into polycarbonate polyols.

Such polycarbonate polyols preferably have number average molar masses of 400 to 4000 g/mol, particularly preferably of 500 to 2000 g/mol. The OH functionality of these polyols is preferably 1.8 to 3.2, particularly preferably 1.9 to 3.0.

Suitable polyether polyols are polyadducts of cyclic ethers with OH— or NH-functional starter molecules, which polyadducts optionally have a block structure.

Suitable cyclic ethers are, for example, styrene oxides, ethylene oxide, propylene oxide, tetrahydrofuran, butylene oxide, epichlorohydrin and any desired mixtures thereof.

Starters which may be used are the polyhydric alcohols mentioned in the context of the polyester polyols and having an OH functionality of ≥2 and primary or secondary amines and amino alcohols.

Preferred polyether polyols are those of the abovementioned type, exclusively based on propylene oxide or random or block copolymers based on propylene oxide with further 1-alkylene oxides, the proportion of the 1-alkylene oxide not being higher than 80% by weight. Propylene oxide homopolymers and random or block copolymers which have oxyethylene, oxypropylene and/or oxybutylene units are particularly preferred, the proportion of the oxypropylene units, based on the total amount of all oxyethylene, oxypropylene and oxybutylene units, accounting for at least 20% by weight, preferably at least 45% by weight. Here, oxypropylene and oxybutylene comprise all respective linear and branched C3- and C4-isomers.

Such polyether polyols preferably have number average molar masses of 250 to 10 000 g/mol, particularly preferably of 500 to 8500 g/mol and very particularly preferably of 600 to 4500 g/mol. The OH functionality is preferably 1.5 to 4.0, particularly preferably 1.8 to 3.1 and very particularly preferably 1.9 to 2.2.

Preferably used special polyether polyols are those which consist of an isocyanate-reactive component comprising hydroxy-functional multiblock copolymers of the type $Y(X_i-H)_n$ with i=1 to 10 and n=2 to 8 and number average molecular weights of greater than 1500 g/mol, the segments Xi each being composed of oxyalkylene units of the formula I,

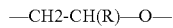

—CH2-CH(R)—O—          formula I in which R is a hydrogen, alkyl, or aryl radical which can also be substituted or may be interrupted by heteroatoms (such as ether oxygens), Y is the underlying starter and the proportion of the segments Xi, based on the total amount of the segments Xi and Y, accounts for at least 50% by weight.

The outer blocks $X_i$ account for at least 50% by weight, preferably 66% by weight, of the total molar mass of $Y(X_i-H)_n$ and consist of monomer units which are of the formula I. Preferably, n in $Y(X_i-H)_n$ is a number from 2 to 6, particularly preferably 2 or 3 and very particularly preferably 2. Preferably, i in $Y(X_i-H)_n$ is a number from 1 to 6, particularly preferably from 1 to 3 and very particularly preferably 1.

In formula I, R is preferably a hydrogen, a methyl, butyl, hexyl or octyl group or an alkyl radical containing ether groups. Preferred alkyl radicals containing ether groups are those based on oxyalkylene units.

The multiblock copolymers $Y(X_i-H)_n$ preferably have number average molecular weights of more than 1200 g/mol, particularly preferably more than 1950 g/mol, but preferably not more than 12 000 g/mol, particularly preferably not more than 8000 g/mol.

The blocks $X_i$ may be homopolymers of exclusively identical oxyalkylene repeating units. They may also have a random structure of different oxyalkylene units or in turn have a block structure comprising different oxyalkylene units.

Preferred, the segments $X_i$ are based exclusively on propylene oxide or random or blockwise mixtures of propylene oxide with further 1-alkylene oxides, the proportion of further 1-alkylene oxides not being higher than 80% by weight.

Propylene oxide homopolymers and random or block copolymers which oxyethylene and/or oxypropylene units are particularly preferred as segments $X_i$, the proportion of the oxypropylene units, based on the total amount of all oxyethylene and oxypropylene units, accounting for at least 20% by weight, preferably at least 40% by weight.

The blocks $X_i$ are, as described further below, added by ring-opening polymerization of the alkylene oxides described above to an n-fold hydroxy- or amino-functional starter block $Y(H)_n$.

The inner block Y, which is present in an amount of less than 50% by weight, preferably of less than 34% by weight, in $Y(X_i-H)_n$, consists of dihydroxy-functional and/or higher hydroxy-functional polymer structures based on cyclic ethers or is composed of dihydroxy-functional and/or higher hydroxy-functional polycarbonate, polyester, poly(meth)acrylate, epoxy resin and/or polyurethane structure units or corresponding hybrids.

Suitable polyester polyols are linear polyesterdiols or branched polyester polyols, as can be prepared in a known manner from aliphatic, cycloaliphatic or aromatic di- or polycarboxylic acids or their anhydrides, such as, for example, succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic or trimellitic acid and acid anhydrides, such as o-phthalic, trimellitic or succinic anhydride or any desired mixtures thereof with polyhydric alcohols, such as, for example, ethanediol, di-, tri- or tetraethylene glycol, 1,2-propanediol, di-, tri- or tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol or mixtures thereof, optionally with concomitant use of higher-functional polyols, such as trimethylolpropane or glycerol. Of course, cycloaliphatic and/or aromatic di- and polyhydroxy compounds are also suitable as polyhydric alcohols for the preparation of the polyester polyols. Instead of the free polycarboxylic acid, it is also possible to use the corresponding polycarboxylic anhydrides or corresponding polycarboxylic esters of low alcohols or mixtures thereof for the preparation of the polyesters.

The polyester polyols may also be based on natural raw materials such as castor oil. It is also possible for the polyester polyols to be based on homo- or copolymers of lactones, as can preferably be obtained by an addition reaction of lactones or lactone mixtures such as butyrolactone, ε-caprolactone and/or methyl-ε-caprolactone, with hydroxy-functional compounds, such as polyhydric alcohols having an OH functionality of preferably 2, for example of the abovementioned type.

Such polyester polyols preferably have number average molar masses of 200 to 2000 g/mol, particularly preferably of 400 to 1400 g/mol.

Suitable polycarbonate polyols are obtainable in the manner known per se by reacting organic carbonates or phosgene with diols or diol mixtures.

Suitable organic carbonates are dimethyl, diethyl and diphenyl carbonate.

Suitable diols or mixtures comprise the polyhydric alcohols mentioned per se in the context of the polyester polyols and having an OH functionality of 2, preferably 1,4-butanediol, 1,6-hexanediol and/or 3-methylpentanediol. Polyester polyols can also be converted into polycarbonate polyols. Dimethyl or diethyl carbonate is particularly preferably used in the reaction of said alcohols to give polycarbonate polyols.

Such polycarbonate polyols preferably have number average molar masses of 400 to 2000 g/mol, particularly preferably of 500 to 1400 g/mol and very particularly preferably of 650 to 1000 g/mol.

Suitable polyether polyols are polyadducts of cyclic ethers with OH— or NH-functional starter molecules, which polyadducts optionally have a block structure. For example, the polyadducts of styrene oxides, of ethylene oxide, propylene oxide, tetrahydrofuran, butylene oxide, epichlorohydrin, and their mixed adducts and graft products and the polyether polyols obtained by condensation of polyhydric alcohols or mixtures thereof and the polyether polyols obtained by alkoxylation of polyhydric alcohols, amines and amino alcohols may be as polyether polyols.

Suitable polymers of cyclic ethers are in particular polymers of tetrahydrofuran.

Starters which may be used are the polyhydric alcohols mentioned per se in the context of the polyester polyols and primary or secondary amines and amino alcohols having an OH or NH functionality of 2 to 8, preferably 2 to 6, particularly preferably 2 to 3, very particularly preferably 2.

Such polyether polyols preferably have number average molar masses of 200 to 2000 g/mol, particularly preferably of 400 to 1400 g/mol and very particularly preferably of 650 to 1000 g/mol.

The polymers of tetrahydrofuran are preferably used as polyether polyols used for starters.

Of course, mixtures of the components described above can also be used for the inner block Y.

Preferred components for the inner block Y are polymers of tetrahydrofuran and aliphatic polycarbonate polyols and polyester polyols and polymers of ε-caprolactone having number average molar masses of less than 3100 g/mol.

Particularly preferred components for the inner block Y are difunctional polymers of tetrahydrofuran and difunctional aliphatic polycarbonate polyols and polyester polyols and polymers of ε-caprolactone having number average molar masses of less than 3100 g/mol.

Very particularly preferably, the starter segment Y is based on difunctional, aliphatic polycarbonate polyols, poly(ε-caprolactone) or polymers of tetrahydrofuran having number average molar masses of greater than 500 g/mol and less than 2100 g/mol.

Preferably used block copolymers of the structure $Y(X_i—H)_n$ consist of more than 50 percent by weight of the blocks $X_i$ described above as and have a number average total molar mass of greater than 1200 g/mol.

Particularly preferred block copolyols consist of less than 50 percent by weight of aliphatic polyester, aliphatic polycarbonate polyol or poly-THF and of more than 50 percent by weight of the blocks $X_i$ described above as being according to the invention and have a number average molar mass of greater than 1200 g/mol. Particularly preferred block copolymers consist of less than 50 percent by weight of aliphatic polycarbonate polyol, poly(ε-caprolactone) or poly-THF and of more than 50 percent by weight of the blocks $X_i$ described above as being according to the invention and have a number average molar mass of greater than 1200 g/mol.

Very particularly preferred block copolymers consist of less than 34 percent by weight of aliphatic polycarbonate polyol, poly(ε-caprolactone) or poly-THF and of more than 66 percent by weight of the blocks $X_i$ described above as being according to the invention and have a number average molar mass of greater than 1950 g/mol and less than 9000 g/mol.

The block copolyols described are prepared by alkylene oxide addition processes. Firstly, the base-catalysed addition reaction of alkylene oxides with starter compounds having Zerewitinoff-active hydrogen atoms $Y(H)_n$ is of industrial importance; secondly, the use of double metal cyanide compounds ("DMC catalysts") for carrying out this reaction the is becoming increasingly important. Hydrogen bonded to N, O or S is designated as Zerewitinoff-active hydrogen (sometimes also only as "active hydrogen") if it is donated according to a process discovered by Zerewitinoff by reaction with methylmagnesium iodide. Typical examples of compounds having Zerewitinoff-active hydrogen are compounds which contain carboxyl, hydroxyl, amino, imino or thiol groups as functional groups. The base-catalysed addition reaction of alkylene oxides, such as, for example, ethylene oxide or propylene oxide, with starter compounds having Zerewitinoff-active hydrogen atoms takes place in the presence of alkali metal hydroxides, but it is also possible to use alkali metal hydrides, alkali metal carboxylates or alkaline earth metal hydroxides. After the addition reaction of the alkylene oxides is complete, the polymerization-active centres on the polyether chains must be deactivated, for example by neutralization with dilute mineral acids, such as sulphuric acid or phosphoric acid, and removal of the resulting salts. In the process according to the invention, DMC catalysts are preferably used. Highly active DMC catalysts which are described, for example, in U.S. Pat. No. 5,470,813, EP-A 700 949, EP-A 743 093, EP-A 761 708, WO 97/40086, WO 98/16310 and WO 00/47649 are particularly preferably used. The highly active DMC catalysts which are described in EP-A 700 949 and, in addition to a double metal cyanide compound (e.g. zinc hexacyano-cobaltate(III)) and an organic complex ligand (e.g. tert-butanol), also contain a polyether having a number average molecular weight of greater than 500 g/mol are a typical example. Owing to their high activity, these catalysts can be used in such small amounts that further working-up of the polyether polyols is not required. The process is described in detail below. The OH-functionalized precursor Y present in an amount of less than 50 percent by weight in the block copolymer is always used as the "starter polyol", onto which alkylene oxide is polymerized so that a multiblock copolymer is obtained in the end. Preferably used alkylene oxides are ethylene oxide, propylene oxide, butylene oxide and mixtures thereof. The synthesis of the polyether chains by alkoxylation can be carried out, for example, only with a monomeric epoxide or can also be effected randomly or blockwise with a plurality of different monomeric epoxides.

Preferred combinations of component a) and b) in the preparation of the matrix polymers are:

A) Adducts of butyrolactone, ε-caprolactone and/or methyl-ε-caprolactone with polyether polyols having a functionality of 1.8 to 3.1 and number average molar masses of 200 to 4000 g/mol in combination with isocyanurates, uretdiones, iminooxadiazinediones and/or other oligomers based on HDI. Particularly preferably adducts of ε-caprolactone with poly(tetrahydrofurans) having a functionality of 1.9 to 2.2 and number average molar masses of 500 to 2000 g/mol (in particular 600 to 1400 g/mol), the number average total molar mass of which is from 800 to 4500 g/mol, in particular from 1000 to 3000 g/mol, in combination with oligomers, isocyanurates and/or iminooxadiazinediones based on HDI.

B) Polyester polyols based on butane-1,4-diol, hexane-1,6-diol, neopentyl glycol, di-, tri- or polyethylene glycol having a number average molar mass of less than 500 g/mol, tri- and/or tetrapropylene glycol in combination with aliphatic di- or polycarboxylic acids or anhydrides, such as adipic acid and/or succinic acid, or mixtures of the abovementioned aliphatic polycarboxylic acids or anhydrides with aromatic polycarboxylic acids or anhydrides, such as terephthalic acid and/or isophthalic acid, the proportion of the aromatic polycarboxylic acids or anhydrides preferably accounting for less than 30 percent by weight, based on the total amount of the polycarboxylic acids or anhydrides used, with number average molar masses of between 1000 and 4000 g/mol and functionalities between 1.9 and 3.0, in combination with oligomers, isocyanurates and/or iminooxadiazinediones based on HDI.

C) Polyether polyols having number average molar masses of 500 to 8500 g/mol and OH functionalities of 1.8 to 3.2, exclusively based on propylene oxide, or random or block copolyols based on propylene oxide and ethylene oxide, the proportion of ethylene oxide not being higher than 60% by weight, in combination with urethanes, allophanates or biurets obtained from aliphatic isocyanate-functional compounds and oligomeric or polymeric isocyanate-reactive compounds having number average molar masses of 200 to 6000 g/mol. Propylene oxide homopolymers having number average molar masses of 1800 to 4500 g/mol and OH functionalities of 1.9 to 2.2 in combination with allophanates obtained from HDI or TMDI and difunctional polyether polyols (in particular polypropylene glycols) having number average molar masses of 200 to 2100 g/mol are particularly preferred.

D) Polyether block or multiblock copolymers of the formula II, in which Y is a purely aliphatic polycarbonate polyol or a polymer of tetrahydrofuran having in each case an OH functionality of 1.8 to 3.1 and a number average molar masses of 400 to 2000 g/mol, n is 2, i is 1 or 2 and R is methyl or H, having a total number average molar mass of 1950 to 9000 g/mol, preferably of 1950 to 6000 g/mol, in combination with urethanes, allophanates or biurets obtained from aliphatic isocyanate-functional compounds and oligomeric or polymeric isocyanate-reactive compounds having number average molar masses of 200 to 6000 g/mol or in combination with isocyanurates, uretdiones, iminooxadiazinediones and/or other oligomers based on HDI. Polyether block or multiblock copolymers of the formula II, in which Y is a purely aliphatic polycarbonate polyol based on 1,4-butanediol and/or 1,6-hexanediol with dimethyl or diethyl carbonate or a polymer of tetrahydrofuran having an OH functionality of 1.8 to 2.2 and a number average molar masses of 600 to 1400 g/mol (in particular up to 1000 g/mol), n is 2, i is 1 or 2 and R is methyl or H, the proportion of ethylene oxide units, based on the total mass of $X_i$, not being higher than 60% by weight, in combination with allophanates obtained from HDI or TMDI and difunctional polyether polyols (in particular polypropylene glycols) having number average molar masses of 200 to 2100 g/mol, in combination with biurets having number average molar masses of 200 to 1400 g/mol (in particular also as a mixture with other oligomers of difunctional aliphatic isocyanates), based on aliphatic diamines or polyamines and aliphatic diisocyanates, in particular HDI and TMDI, in combination with urethanes obtained from HDI or TMDI and based on adducts of butyrolactone, ε-caprolactone and/or methyl-ε-caprolactone (in particular ε-caprolactone) with aliphatic, araliphatic or cycloaliphatic di-, tri- or polyfunctional alcohols containing 2 to 20 carbon atoms (in particular with difunctional aliphatic alcohols having 3 to 12 carbon atoms), having number average molar masses of 200 to 3000 g/mol, particularly preferably of 1000 to 2000 g/mol (in particular as a mixture with other oligomers of difunctional aliphatic isocyanates) or in combination with isocyanurates, iminooxadiazinediones and/or other oligomers based on HDI are particularly preferred.

One or more different compounds which have groups reacting under the action of actinic radiation with ethylenically unsaturated compounds with polymerization (radiation-curing groups) and are themselves free of NCO groups are used as component B). The writing monomers acrylates and/or methacrylates are preferred.

In component B), compounds such as α,β-unsaturated carboxylic acid derivatives, such as acrylates, methacrylates, maleates, fumarates, maleimides, acrylamides, furthermore vinyl ethers, propenyl ethers, allyl ethers and compounds containing dicyclopentadienyl units and olefinically unsaturated compounds, such as, for example, styrene, α-methylstyrene, vinyltoluene, olefins, such as, for example, 1-octene and/or 1-decene, vinyl esters, (meth)acrylonitrile, (meth)acrylamide, methacrylic acid, acrylic acid, can be used. Acrylates and methacrylates are preferred.

In general, esters of acrylic acid or methacrylic acid are designated as acrylates and methacrylates, respectively. Examples of acrylates and methacrylates which can be used are methyl acrylate, methyl methacrylate, ethyl acrylate, ethyl methacrylate, ethoxyethyl acrylate, ethoxyethyl methacrylate, n-butyl acrylate, n-butyl methacrylate, tert-butyl acrylate, tert-butyl methacrylate, hexyl acrylate, hexyl methacrylate, 2-ethylhexyl acrylate, 2-ethylhexyl methacrylate, butoxyethyl acrylate, butoxyethyl methacrylate, lauryl acrylate, lauryl methacrylate, isobornyl acrylate, isobornyl methacrylate, phenyl acrylate, phenyl methacrylate, p-chlorophenyl acrylate, p-chlorophenyl methacrylate, p-bromophenyl acrylate, p-bromophenyl methacrylate, 2,4,6-trichlorophenyl acrylate, 2,4,6-trichlorophenyl methacrylate, 2,4,6-tribromophenyl acrylate, 2,4,6-tribromophenyl methacrylate, pentachlorophenyl acrylate, pentachlorophenyl methacrylate, pentabromophenyl acrylate, pentabromophenyl methacrylate, pentabromobenzyl acrylate, pentabromobenzyl methacrylate, phenoxyethyl acrylate, phenoxyethyl methacrylate, phenoxyethoxyethyl acrylate, phenoxyethoxyethyl methacrylate, 2-naphthyl acrylate, 2-naphthyl methacrylate, 1,4-bis(2-thionaphthyl)-2-butyl acrylate, 1,4-bis(2-thionaphthyl)-2-butyl methacrylate, propane-2,2-diylbis[(2,6-dibromo-4,1-phenylen)oxy(2-{[3,3,3-tris(4-chlorophenyl)propanoyl]oxy}propane-3,1-diyl)oxyethane-2,1-diyl] diacrylate, bisphenol A diacrylate, bisphenol A dimethacrylate, tetrabromobisphenol A diacrylate, tetrabromobisphenol A dimethacrylate and the ethoxylated analogue compounds thereof, N-carbazolyl acrylates to mention but a selection of acrylates and methacrylates which can be used.

Of course, urethane acrylates can also be used as component B). Urethane acrylates are understood as meaning compounds having at least one acrylate group which additionally have at least one urethane bond. It is known that such compounds can be obtained by reacting a hydroxy-functional acrylate with an isocyanate-functional compound.

Acrylates and methacrylates having a refractive index $n_D^{20}$ (as measured at a wavelength of 405 nm) of greater than 1.450 are preferably used. Acrylates which contain at least one aromatic structural unit and have a refractive index $n_D^{20}$ (405 nm) of greater than 1.500 are particularly preferably used. Acrylates and methacrylates based on bisphenol A or derivatives thereof and those acrylates and methacrylates which contain a thioaryl group may be mentioned as particularly suitable examples thereof.

Examples of the urethane acrylates and/or urethane methacrylates used as component B) are the adducts of aromatic triisocyanates (very particularly preferably tris(4-phenylisocyanato) thiophosphate, or trimers of aromatic diisocyanates, such as toluene diisocyanate) with hydroxyethyl acrylate, hydroxypropyl acrylate, 4-hydroxybutyl acrylate, the adducts of 3-thiomethylphenyl isocyanate with hydroxyethyl acrylate, hydroxypropyl acrylate, 4-hydroxybutyl acrylate and unsaturated glycidyl ether acrylate urethanes (as described in the applications WO 2008/125229 A1 and in the non-prior-published application EP 09009651.2) or any desired mixtures thereof with one another.

A further preferred embodiment uses, as writing monomers, a combination of a monofunctional and a polyfunctional writing monomer.

The monofunctional writing monomer may have in particular the general formula (II)

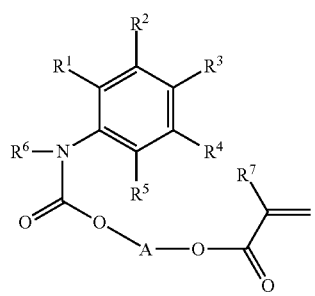

(II)

in which $R^1$, $R^2$, $R^3$, $R^4$, $R^5$, in each case independently of one another, are a hydrogen or halogen atom or a C1-C6-alkyl, trifluoromethyl, C1-C6-alkylthio, C1-C6-alkylseleno, C1-C6-alkyltelluro or nitro group, with the proviso that at least one substituent of the group $R^1$, $R^2$, $R^3$, $R^4$, $R^5$ is not hydrogen, $R^6$, $R^7$, in each case by themselves, are hydrogen or a C1-C6-alkyl group and A is a saturated or unsaturated or linear or branched C1-C6-alkyl radical or a polyethylene oxide radical or a polypropylene oxide radical having in each case 2-6 repeating units in the polymer chain, and the monofunctional writing monomer preferably has a glass transition temperature $T_G$ of <0° C. and preferably a refractive index of >1.50 at 405 nm.

The polyfunctional writing monomer may have, in particular, the general formula (III)

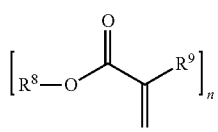

(III)

in which n is ≥2 and n is ≤4 and $R^8$, $R^9$ are hydrogen and/or, independently of one another, linear, branched, cyclic or heterocyclic organic radicals which are unsubstituted or optionally also substituted by heteroatoms. Furthermore, the polyfunctional writing monomer may preferably have a refractive index of >1.50 at 405 nm.

One or more photoinitiators are used as component C). These are usually initiators which can be activated by actinic radiation and initiate polymerization of the corresponding polymerizable groups. Photoinitiators are commercially distributed compounds known per se, a distinction being made between monomolecular (type I) and bimolecular (type II) initiators. Furthermore, depending on the chemical nature, these initiators are used for free radical, anionic (or) cationic (or mixed) forms of the abovementioned polymerizations.

(Type I) systems for free radical photopolymerization are, for example, aromatic ketone compounds, e.g. benzophenones in combination with tertiary amines, alkylbenzophenones, 4,4'-bis(dimethylamino)benzophenone (Michler's ketone), anthrone and halogenated benzophenones or mixtures of said types. More suitable are (type II) initiators such as benzoin and its derivatives, benzil ketals, acylphosphine oxides e.g. 2,4,6-trimethylbenzoyl-diphenylphosphine oxide, bisacylophosphine oxides, phenylglyoxylic acid esters, campherquinone, alpha-aminoalkylphenones, alpha, alpha-dialkoxyacetophenones, 1-[4-(phenylthio)phenyl]octane-1,2-dione 2-(O-benzoyloxime), differently substituted hexarylbisimidazoles (HABI) with suitable coinitiators, such as, for example, mercaptobenzoxazole, and alpha-hydroxyalkylphenones. The photoinitiator systems described in EP-A 0223587 and consisting of a mixture of an ammonium arylborate and one or more dyes can also be used as a photoinitiator. For example, tetrabutylammonium triphenylhexylborate, tetrabutylammonium triphenylbutylborate, tetrabutylammonium trinaphthylbutylborate, tetramethylammonium triphenylbenzylborate, tetra(n-hexyl)ammonium (sec-butyl) triphenylborate, 1-methyl-3-octylimidazolium dipentyldiphenylborate, tetrabutylammonium tris(4-tert-butyl)phenylbutylborate, tetrabutylammonium tris(3-fluorophenyl)hexylborate and tetrabutylammonium tris(3-chloro-4-methylphenyl)hexylborate are suitable as an ammonium arylborate. Suitable dyes are, for example, new methylene blue, thionine, basic yellow, pinacynol chloride, rhodamine 6G, gallocyanine, ethyl violet, Victoria blue R, celestine blue, quinaldine red, crystal violet, brilliant green, astrazone orange G, darrow red, pyronine Y, basic red 29, pyrillium I, safranine O, cyanine and methylene blue, azur A (Cunningham et al., RadTech '98 North America UV/EB Conference Proceedings, Chicago, Apr. 19-22, 1998).

The photoinitiators used for the anionic polymerization are as a rule (type I) systems and are derived from transition metal complexes of the first series. Chromium salts, such as trans-$Cr(NH_3)_2(NCS)_4$ (Kutal et al, Macromolecules 1991, 24, 6872) or ferrocenyl compounds (Yamaguchi et al., Macromolecules 2000, 33, 1152), are here. A further possibility of anionic polymerization consists in the use of dyes, such as crystal violet leuconitrile or malchite green leuconitrile, which can polymerize cyanoacrylates by photolytic decomposition (Neckers et al., Macromolecules 2000, 33, 7761). However, the chromophore is incorporated into the polymer thereby, so that the resulting polymers are coloured throughout.

The photoinitiators used for the cationic polymerization substantially consist of three classes: aryldiazonium salts, onium salts (here specifically: iodonium, sulphonium and selenonium salts) and organometallic compounds. With irradiation, both in the presence and in the absence of a hydrogen donor, phenyldiazonium salts can produced a cation that initiates the polymerization. The efficiency of the overall system is determined by the nature of the counterion used for the diazonium compound. SbF6-, AsF6- or PF6- which have little reactivity and are very expensive are preferred here. These compounds are as a rule not very suitable for use in the coating of thin films since the surface quality is reduced (pinholes) the nitrogen released after the exposure (Li et al., Polymeric Materials Science and Engineering, 2001, 84, 139). Onium salts, especially sulphonium and iodonium salts, are very widely used and also commercially available in many forms. The photochemistry of these compounds has long been investigated. The iodonium salts decompose after excitation, initially homolytically, and thus produce a free radical and a radical anion which is stabilized by H abstraction and liberates a proton and then initiates the cationic polymerization (Dektar et al. J. Org. Chem. 1990, 55, 639; J. Org. Chem., 1991, 56. 1838). This mechanism permits the use of iodonium salts also for free radical photopolymerization. Here again, the choice of the counterion is of considerable importance, and $SbF_6^-$, $AsF_6^-$ or $PF_6^-$ is likewise preferred. Otherwise, the choice of the substitution of the aromatic is entirely free in this structure class and substantially determined by the availability of suitable starting building blocks for the synthesis. The sulphonium salts are compounds which decompose in according to Norrish(II) (Crivello et al., Macromolecules, 2000, 33, 825). In the case of the sulphonium salts too, the choice of the counterion is of critical importance, which manifests itself substantially in the curing rate of the polymers. The best results are obtained as a rule with $SbF_6^-$-salts. Since the self-absorption of iodonium and sulphonium salts occurs at <300 nm, these compounds must be accordingly sensitized for photopolymerization with near UV or shortwave visible light. This is effected by the use of more highly absorbing aromatics, for example, anthracene and derivatives (Gu et al., Am. Chem. Soc. Polymer Preprints, 2000, 41 (2), 1266) or phenothiazine or derivatives thereof (Hua et al, Macromolecules 2001, 34, 2488-2494).

It may be advantageous also to use mixtures of these compounds. Depending on the radiation source used for curing, type and concentration of photoinitiator must be adapted in a manner known to the person skilled in the art. Further details are described, for example, in P. K. T. Oldring (Ed.), Chemistry & Technology of UV & EB Formulations For Coatings, Inks & Paints, Vol. 3, 1991, SITA Technology, London, pages 61-328.

Preferred photoinitiators C) are mixtures of tetrabutylammonium triphenylhexylborate, tetrabutylammonium triphenylbutylborate, tetrabutylammonium trinaphthylbutylborate, tetrabutylammonium tris (4-tert-butyl)phenylbutylborate, tetrabutylammonium tris(3-fluorophenyl)hexylborate and tetrabutylammonium tris(3-chloro-4-methylphenyl)hexylborate with dyes such as, for example, astrazone orange G, methylene blue, new methylene blue, azur A, pyrillium I, safranine O, cyanine, gallocyanine, brilliant green, crystal violet, ethyl violet and thionine.

The photoinitiator system used can preferably comprise an anionic, cationic or neutral dye and a coinitiator.

The photopolymer formulation may additionally contain urethanes as plasticizers (component D), where the urethanes may preferably be substituted by at least one fluorine atom.

The urethanes are preferably compounds which have a structural element with the general formula IV.

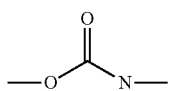

Formula IV

They can be obtained from monofunctional alcohols and monofunctional isocyanates as described above. They are preferably substituted by at least one fluorine atom.

It is further preferred if the fluorourethanes have the general formula V

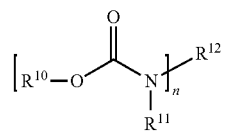

Formula V in which n is ≥1 and n is ≤8 and $R^{10}$, $R^{11}$, $R^{12}$ are hydrogen and/or, independently of one another, linear, branched, cyclic or heterocyclic organic radicals which are unsubstituted or optionally also substituted by heteroatoms, at least one of the radicals $R^{10}$, $R^{11}$, $R^{12}$ being substituted by at least one fluorine atom. Here, $R^{10}$ is particularly preferably an organic radical having at least one fluorine atom.

According to a further embodiment, $R^{10}$ may comprise 1-20 $CF_2$ groups and/or one or more $CF_3$ groups, particularly preferably 1-15 $CF_2$ groups and/or one or more $CF_3$ groups, particularly preferably 1-10 $CF_2$ groups and/or one or more $CF_3$ groups, very particularly preferably 1-8 $CF_2$ groups and/or one or more $CF_3$ groups, $R^{11}$ may comprise a C1-C20 alkyl radical, preferably a C1-C15 alkyl radical, particularly preferably a C1-C10 alkyl radical, or hydrogen, and/or $R^{12}$ may comprise a C1-C20 alkyl radical, preferably a C1-C15 alkyl radical, particularly preferably a C1-C10 alkyl radical or hydrogen.

The fluorourethanes may have a fluorine content of 10-80% by weight of fluorine, preferably of 13-70% by weight of fluorine and particularly preferably 17.5-65% by weight of fluorine.

Further constituents of the photopolymer formulation as component E) may be: free radical stabilizers, optionally catalysts or other auxiliaries and additives.

Inhibitors and antioxidants, as described, for example, in "Methoden der organischen Chemie [Methods of Organic Chemistry]" (Houben-Weyl), 4th Edition, Vol. XIV/1, page 433 et seq., Georg Thieme Verlag, Stuttgart 1961, are suitable as examples of free radical stabilizers. Suitable classes of substances are, for example, phenols, such as, for example, 2,6-di-tert-butyl-4-methylphenol, cresols, hydroquinones, benzyl alcohols, such as, for example, benzhydrol, optionally also quinones, such as, for example, 2,5-di-tert-butylquinone, optionally also aromatic amines such as diisopropylamine or phenothiazine.

2,6-Di-tert-butyl-4-methylphenol, phenothiazine, p-methoxyphenol, 2-methoxy-p-hydroquinone and benzhydrol are preferred.

Optionally, one or more catalysts may be used. These are catalysts for accelerating the urethane formation. Known catalysts for this purpose are, for example, tin octoate, zinc octoate, dibutyltin dilaurate, dimethylbis [(1-oxoneodecyl)oxy]stannane, dimethyltin dicarboxylate, zirconium bis(ethylhexanoate), zirconium acetylacetonate or tertiary amines, such as, for example, 1,4-diazabicyclo[2.2.2]octane, diazabicyclononane, diazabicycloundecane, 1,1,3,3-tetramethylguanidine, 1,3,4,6,7,8-hexahydro-1-methyl-2H-pyrimido(1,2-a)pyrimidine.

Dibutyltin dilaurate, dimethylbis[(1-oxoneodecyl)oxy]stannane, dimethyltin dicarboxylate, 1,4-diazabicyclo[2.2.2]octane, diazabicyclononane, diazabicycloundecane, 1,1,3,3- tetramethylguanidine, 1,3,4,6,7,8-hexahydro-1-methyl-2H-pyrimido(1,2-a)pyrimidine are preferred.

Of course, further auxiliaries or additives can optionally be used. These may be, for example, additives customary in the area of coating technology, such as solvents, plasticizers, levelling agents or adhesion promoters. It can also be advantageous to use a plurality of additives of one type simultaneously. Of course, it may also be advantageous to use a plurality of additives of a plurality of types.

According to a further preferred embodiment of the invention, it is intended for the photopolymer formulation to contain 10 to 89.999% by weight, preferably 25 to 70% by weight, of matrix polymers, 10 to 60% by weight, preferably 25 to 50% by weight, of writing monomers, 0.001 to 5% by weight of photoinitiators and optionally 0 to 4% by weight, preferably 0 to 2% by weight, of catalysts, 0 to 5% by weight, preferably 0.001 to 1% by weight, of radical stabilizers, 0 to 30% by weight, preferably 0 to 25% by weight, of plasticizers and 0 to 5% by weight, preferably 0.1 to 5% by weight, of further additives, the sum of all constituents being 100% by weight.

Photopolymer formulations comprising 25 to 70% by weight of matrix polymers consisting of compounds of component a) and of component b), 25 to 50% by weight of writing monomers, 0.001 to 5% by weight of photoinitiators, 0 to 2% by weight of catalysts, 0.001 to 1% by weight of free radical stabilizers, optionally 0 to 25% by weight of the urethanes described above and optionally 0.1 to 5% by weight of further additives are particularly preferably used.

A film comprising the photopolymer formulation can be applied to a substrate in the form of a substrate film, for example with the aid of a roll coating unit.

This can be effected by a combination of different process steps in which positive metering pumps known to the person skilled in the art, vacuum devolatilizers, plate filters, static mixers, slot nozzles and various knifecoating systems, single-roll unwinders, dryers, dry lamination device and a single-roll winding device are used. In particular, a coating devices which have, for example, slot nozzles and knifecoating systems are suitable for the application of liquid photopolymer formulations to moving substrate materials and are distinguished by high accuracy in the applied layer thickness.

In a preferred embodiment, the process for coating the substrate film comprises the following individual steps for the treatment of abovementioned photopolymer compounds:
I. transport and metering firstly of the component a), optionally mixed with one or more of the components B), C), D) and E), and secondly, separately therefrom, of the component b), optionally mixed with one or more of the components B), C), D) and E)
II. devolatilization of the streams transported, metered and optionally premixed according to I)
III. filtration of the mixture obtained according to II)
IV. homogenization of the mixture obtained according to III)
V. unwinding and pre-treatment of the substrate material
VI. coating of the substrate material with the mixture obtained according to step IV)
VII. drying of the film coated according to VI)
VIII. lamination of the coated film obtained according to VII)
IX. winding up of the laminated film obtained according to VIII)

Further preferred embodiment of the process are disclosed in the already cited, as yet unpublished European Application EP 09001952.2.

FIG. 1 shows the schematic setup of a typical coating unit, including the arrangement of the pre-treatment of the coating material (1-5), the schematic path of the substrate material (8+9), the coating device for application to a substrate material (6) and the subsequent drying process (7).

Designations in FIG. 1:
1 Storage container
2 Metering device
3 Vacuum devolatilization
4 Filter
5 Static mixer
6 Coating device
7 Dryer
8 Web path
9 Product lamination By combining the process steps shown in FIG. 1, greater accuracy of layer thickness is achieved at applied photopolymer layer thicknesses on moving substrate materials.

According to a further preferred embodiment, the holographic films may be film composites which may consist of one or more substrate films, one or more photopolymer films and one or more protective films in any desired arrangement.

Preferred materials or material composites of the substrate layer are based on polycarbonate (PC), polyethylene terephthalate (PET), polybutylene terephthalate, polyethylene, polypropylene, cellulose acetate, cellulose hydrate, cellulose nitrate, cycloolefin polymers, polystyrene, polyepoxides, polysulphone, cellulose triacetate (CTA), polyamide, polymethyl methacrylate, polyvinyl chloride, polyvinyl butyral or polydicyclopentadiene or mixtures thereof. In addition, material composites, such as film laminates or coextrudates, can be used as substrate film. Examples of material composites are duplex and triplex films having a structure according to one of the schemes A/B, A/B/A or A/B/C, such as PC/PET, PET/PC/PET and PC/TPU (TPU=thermoplastic polyurethane). PC and PET are particularly preferably used as substrate film.

Transparent substrate films which are optically clear, i.e. not hazy, are preferred. The haze is measurable via the haze value, which is less than 3.5%, preferably less than 1%, particularly preferably less than 0.3%.

The haze value describes the fraction of transmitted light which is scattered in a forward direction by the sample through which radiation has passed. Thus, it is a measure of the opacity or haze of transparent materials and quantifies material defects, particles, inhomogeneities or crystalline phase boundaries in the material or its surface which interfere with the transparency. The method for measuring the haze is described in the standard ASTM D 1003.

Preferably, the substrate film has an optical retardation which is not too high, i.e. a mean optical retardation of less than 1000 nm, preferably of less than 700 nm, particularly preferably of less than 300 nm, is typically present. The automatic and objective measurement of the optical retardation is effected using an imaging polarimeter, for example from ilis GmbH, StainMatic® M3/M model. The optical retardation is measured in perpendicular incidence. The retardation values stated for the substrate film are lateral mean values.

The substrate film, including possible coatings on one or both sides, typically has a thickness of 5 to 2000 µm, preferably 8 to 300 µm, particularly preferably 30 to 200 µm and in particular 125 to 175 µm or 30 to 45 µm.

In addition to the constituents and can for the film composite have one or more covering layers on the photopolymer layer in order to protect it from dirt and environmental influences. Plastics films or film composite systems, but also clearcoats can be used for this purpose.

Preferably used covering layers are film materials analogous to the materials used in the substrate film, these a thickness of typically 5 to 200 µm, preferably 8 to 125 µm, particularly preferably 20 to 50 µm.

Covering layers having as smooth a surface as possible are preferred. The roughness determined according to DIN EN ISO 4288, "Geometrical Product Specifications (GPS)-Surface texture . . . ", test condition R3z front and back, is used as a measure. Preferred roughnesses are in the region of less than or equal to 2 µm, preferably less than or equal to 0.5 µm.

PE or PET films having a thickness of 20 to 60 µm are preferably used as laminating films; a polyethylene film of 40 µm thickness is particularly preferably used.

Further protective layers, for example a backing of the substrate film, may be used.

The invention furthermore relates to the printability of the photopolymer formulations described. Printing processes are generally understood as meaning procedures and working methods for replicating two-dimensional originals. For example, relief printing, planographic printing, gravure printing, screen printing, pack printing or stamping can be used as possible printing processes. Moreover, newer digital printing techniques, for example, piezo printers or bubble jet printers, can also be used.

The invention furthermore relates to a holographic film obtainable by the process according to the invention.

The present invention still further relates to the use of the holographic films for recording visual holograms, for the production of optical elements, images, representations and a method for recording holograms with the use of the holographic films.

With the holographic films, holograms for optical applications in the entire visible range and in the near UV range (300-800 nm) can be produced by appropriate exposure processes. Visual holograms comprise all holograms which can be recorded by methods known to the person skilled in the art, including, inter alia, in-line (Gabor) holograms, off-axis holograms, full-aperture transfer holograms, white light transmission holograms ("rainbow holograms"), Denisyuk holograms, off-axis reflection holograms, edge-lit holograms and holographic stereograms; reflection holograms, Denisyuk holograms, transmission holograms are preferred. Optical elements, such as lenses, mirrors, deflection mirrors, filters, diffuser screens, diffraction elements, light conductors, waveguides, projection screens and/or masks, are preferred. Frequently, these optical elements show a frequency selectivity, depending on how the holograms were illuminated and on the dimensions of the hologram.

In addition, holographic images or representations, such as, for example, for personal portraits, biometric representations in security documents, or generally of images or image structures for advertising, security labels, trademark protection, trademark branding, labels, design elements, decorations, illustrations, multi journey tickets, images and the like and images which can represent digital data, inter alia also in combination with the products described above, can also be produced by means of the holographic films. Holographic images may give the impression of a three-dimensional image but they may also represent image sequences, short films or a number of different objects, depending on from which angle, with which light source (including moving light source), etc. that is illuminated. Owing to these varied design possibilities, holograms, in particular volume holograms, are an attractive technical solution for the abovementioned application.

EXAMPLES

The following examples serve for explaining the invention. Unless noted otherwise, all stated percentages are based on percent by weight.

Designations which are Used Below:
Photopolymer formulations comprising:
three-dimensionally crosslinked organic matrix polymers A). Particularly preferred three-dimensionally crosslinked polymers are those which are composed of an isocyanate component a)
and an isocyanate-reactive component b) as precursors and
are crosslinked with the aid of a catalyst component E) which as a rule is added in solution,
writing monomers B) which have groups which react under the action of actinic radiation with ethylenically unsaturated compounds with polymerization (radiation-curing groups) and are dissolved or distributed in this matrix
at least one photoinitiator system C)
optionally a non-photopolymerizable component D)
optionally catalysts, free radical stabilizers, solvents, additives and other auxiliaries and/or additives E)

Methods of Measurement:

The stated OH numbers were determined according to DIN 53240-2.

The stated NCO values (isocyanate contents) were determined according to DIN EN ISO 11909.

For the determination of the viscosity, the component or mixture to be investigated was applied in a cone-on-plate measuring system of a rheometer (from Anton Paar Physica Model MCR 51), at 20° C., unless stated otherwise. The measurement is carried out under the following conditions:
Measuring body: cone CP 25, d=25 mm, angle=1°
Measuring gap as distance between cone and plate: 0.047 mm
Duration of measurement: 10 sec.
Determination of viscosity at a shear rate of 250 l/sec.

Determination of the TGA95 Value

The TGA 95 values of the individual components can be determined by weighing an amount of about 10 mg of the sample of the respective component into a small aluminium pan having a volume of 70 µl, introducing the small aluminium pan an oven of a thermobalance, preferably a TG50 thermobalance from Mettler-Toledo, and measuring the loss of mass of the sample in the open small aluminium pan at a constant oven heating rate of 20 K/min, the start temperature of the oven being 30° C. and the end temperature 600° C., flushing the oven with a 200 ml/min nitrogen stream during the determination and determining, as a TGA 95 value of the respective component, the temperature at which a loss of mass of the sample of 5% by weight, based on the originally weighed in amount of sample, has occurred.

Measurement of the Holographic Properties DE and Δn of the Holographic Media by Means of Two-Beam Interference in a Reflection Arrangement For measuring the holographic performance, the protective film of the holographic film is peeled off and the holographic film is laminated on the photopolymer side onto a 1 mm thick glass plate suitable in length and width using a rubber roller with gentle pressure. This sandwich comprising glass and photopolymer film can now be used to determine the holographic performance parameters DE and Δn.

The beam of an He—Ne laser (emission wavelength 633 nm) was converted with the aid of the spatial filter (SF) and together with the collimation lens (CL) into a parallel homogenous beam. The final cross sections of the signal and reference beam are established by the iris diaphragms (I). The diameter of the iris diaphragm opening is 0.4 cm. The polarization-dependent beam splitters (PBS) split the laser beam into two coherent equally polarized beams. Via the λ/2 plates, the power of the reference beam was adjusted to 0.5 mW and the power of the signal beam to 0.65 mW. The powers were determined using the semiconductor detectors (D) with sample removed. The angle of incidence ($\alpha_0$) of the reference beam is −21.8° and the angle of incidence ($\beta_0$) of the signal beam is 41.8°. The angles are measured starting from the sample normal to the beam direction. According to FIG. 3, $\alpha_0$ therefore has a negative sign and $\beta_0$ a positive sign. At the location of the sample (medium), the interference field of the two overlapping beams produced a grating of light and dark strips which are perpendicular to the angle bisector of the two beams incident on the sample (reflection hologram). The strip spacing $\Lambda$, also referred to as grating period, in the medium is ~225 nm (the refractive index of the medium assumed to be ~1.504).

Figure 3:
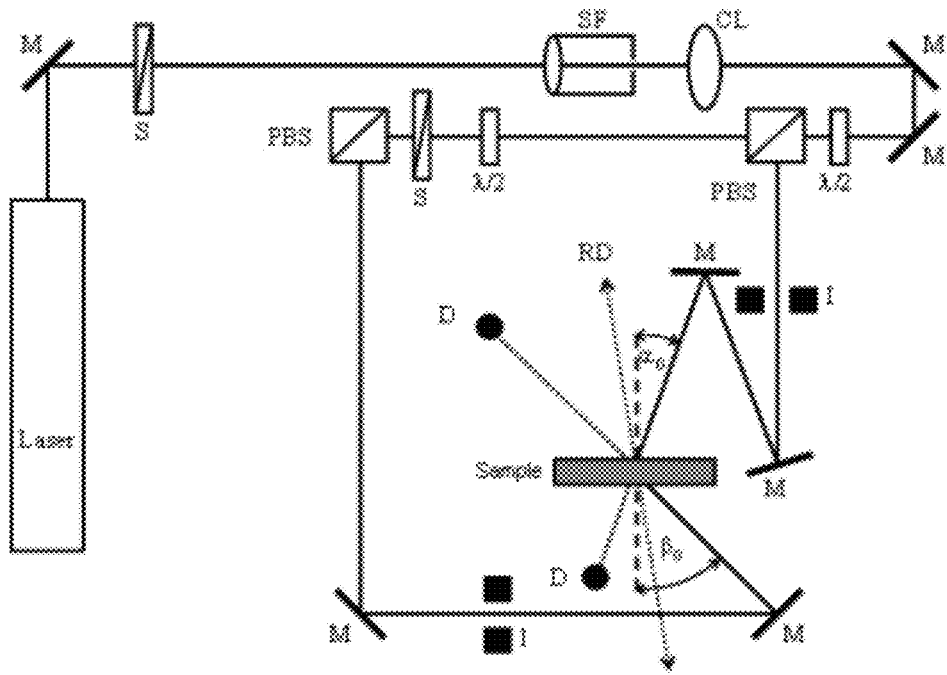
FIG. 3 illustrates the holographic experimental setup with which the diffraction efficiency (DE) of the media was measured.

FIG. 3 shows the holographic experimental setup with which the diffraction efficiency (DE) of the media was measured.

Holograms were written into the medium in the following manner:

Both shutters (S) are opened for the exposure time t.
Thereafter, with closed shutters (S), the medium was allowed a time of 5 minutes for the diffusion of the still unpolymerized writing monomers.

The recorded holograms were read in the following manner. The shutter of the signal beam remained closed. The shutter of the reference beam was opened. The iris diaphragm of the reference beam was closed to a diameter of <1 mm. This ensured that the beam was always completely in the previously written hologram for all angles ($\Omega$) of rotation of the medium. The turntable, under computer control, covered the angle range from $\Omega_{min}$ to $\Omega_{max}$ with an angle step width of 0.05°. $\Omega$ is measured from the sample normal to the reference direction of the turntable. The reference direction of the turntable occurs when, during recording of the hologram, the angle of incidence of the reference beam and of the signal beam are of equal magnitude, i.e. $\alpha_0$=−31.8° and $\beta_0$=31.8°. $\Omega_{recording}$ is then 0°. For $\alpha_0$=−21.8° and $\beta_0$=41.8°, $\Omega_{recording}$ is therefore 10°. The following is generally true for the interference field during recording of the hologram:

$$\alpha_0=\theta_0+\Omega_{recording}.$$

$\theta_0$ is the semiangle in the laboratory system outside the medium and the following is true during recording of the hologram:

$$\theta_0 = \frac{\alpha_0 - \beta_0}{2}.$$

In this case, $\theta_0$ is therefore −31.8°. At each angle $\Omega$ of rotation approached, the powers of the beam transmitted in the zero order were measured by means of the corresponding detector D and the powers of the beam diffracted in the first order were measured by means of the detector D. At each angle $\Omega$ approached, the diffraction efficiency was obtained as the quotient of:

$$\eta = \frac{P_D}{P_D + P_T}$$

$P_D$ is the power in the detector of the diffracted beam and $P_T$ is the power in the detector of the transmitted beam.

By means of the method described above, the Bragg curve (it describes the diffraction efficiency $\eta$ as a function of the angle $\Omega$ of rotation of the recorded hologram) was measured and was stored in a computer. In addition, the intensity transmitted in the zero order was also plotted against the angle $\Omega$ of rotation and was stored in a computer.

The maximum diffraction efficiency (DE=$\eta_{max}$) of the hologram, i.e. its peak value, was determined at $\Omega_{reconstruction}$. For this purpose, the position of the detector of the diffracted beam was changed if necessary, in order to determine this maximum value.

The refractive index contrast $\Delta n$ and the thickness d of the photopolymer layer were now determined by means of the coupled wave theory (c.f. H. Kogelnik, The Bell System Technical Journal, Volume 48, November 1969, Number 9 page 2909-page 2947) from the measured Bragg curve and the angle variation of the transmitted intensity. It should be noted that, owing to the thickness shrinkage occurring as a result of the photopolymerization, the strip spacing $\Lambda'$ of the hologram and the orientation of the strips (slant) may deviate from the strip spacing $\Lambda$ of the interference pattern and the orientation thereof. Accordingly, the angle $\alpha_0'$ or the corresponding angle of the turntable $\Omega_{reconstruction}$ at which maximum diffraction efficiency is achieved will also deviate from $\alpha_0$ or from the corresponding $\Omega_{recording}$, respectively. As a result, the Bragg condition changes. This change is taken into account in the evaluation method. The evaluation method is described below:

All geometrical quantities which relate to the recorded hologram and not to the interference pattern are represented as dashed quantities.

According to Kogelnik, the following is true for the Bragg curve $\eta(\Omega)$ of a reflection hologram:

$$\eta = \begin{cases} \dfrac{1}{1 - \dfrac{1-(\xi/\nu)^2}{\sin^2\left(\sqrt{\xi^2 - \nu^2}\right)}}, & \text{for } \nu^2 - \xi^2 < 0 \\[2ex] \dfrac{1}{1 + \dfrac{1-(\xi/\nu)^2}{\sinh^2\left(\sqrt{\nu^2 - \xi^2}\right)}}, & \text{for } \nu^2 - \xi^2 \geq 0 \end{cases}$$

with:

$$\nu = \frac{\pi \cdot \Delta n \cdot d'}{\lambda \cdot \sqrt{|c_s \cdot c_r|}}$$

$$\xi = -\frac{d'}{2 \cdot c_s} \cdot DP$$

$$c_s = \cos(\vartheta') - \cos(\psi') \cdot \frac{\lambda}{n \cdot \Lambda'}$$

$$c_r = \cos(\vartheta')$$

$$DP = \frac{\pi}{\Lambda'} \cdot \left(2 \cdot \cos(\psi' - \vartheta') - \frac{\lambda}{n \cdot \Lambda'}\right)$$

$$\psi' = \frac{\beta' + \alpha'}{2}$$

$$\Lambda' = \frac{\lambda}{2 \cdot n \cdot \cos(\psi' - \alpha')}$$

When reading the hologram ("reconstruction"), the situation is analogous to that described above:

$$\theta'_0=\theta_0+\Omega$$

$$\sin(\theta'_0)=n\cdot\sin(\theta')$$

At the Bragg condition, the dephasing DP is 0. Accordingly, the following is true:

$$\alpha'_0 = \theta_0 + \Omega_{reconstruction}$$

$$\sin(\alpha'_0) = n \cdot \sin(\alpha')$$

The still unknown angle β' can be determined from the comparison of the Bragg condition of the interference field during recording of the hologram and the Bragg condition during reading of the hologram, assuming that only thickness shrinkage takes place. The following is then true:

$$\sin(\beta') = \frac{1}{n} \cdot [\sin(\alpha_0) + \sin(\beta_0) - \sin(\theta_0 + \Omega_{reconstruction})]$$

ν is the grating thickness, ξ is the detuning parameter and ψ' is the orientation (slant) of the refractive index grating which was recorded. α' and β' correspond to the angles $\alpha_0$ and $\beta_0$ of the interference field during recording of the hologram, but measured in the medium and applicable to the grating of the hologram (after thickness shrinkage). n is the mean refractive index of the photopolymer and was set at 1.504. λ is the wavelength of the laser light in vacuo.

The maximum diffraction efficiency (DE=$\eta_{max}$) for ξ=0 is then:

$$DE = \tanh^2(\nu) = \tanh^2\left(\frac{\pi \cdot \Delta n \cdot d'}{\lambda \cdot \sqrt{\cos(\alpha') \cdot \cos(\alpha' - 2\psi)}}\right)$$

Figure 4:
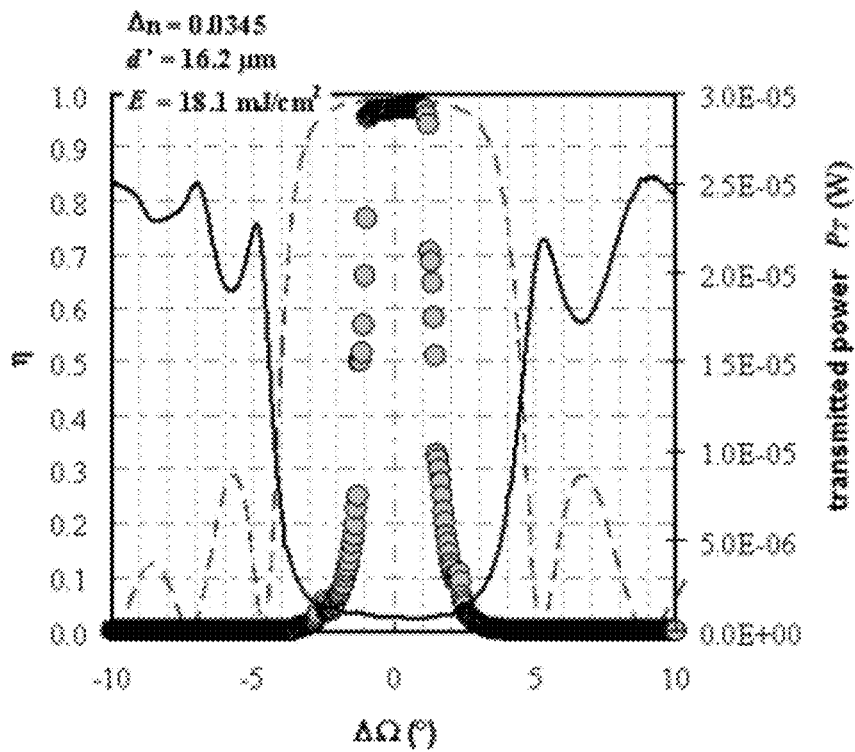
FIG. 4 illustrates a graph showing the measured data of the diffraction efficiency, the theoretical Bragg curve and the transmitted intensity plotted against the angle detuning.

The measured data of the diffraction efficiency, the theoretical Bragg curve and the transmitted intensity are plotted against the centred angle of rotation $\Delta\Omega = \Omega_{reconstruction} - \Omega = \alpha'_0 - \theta'_0$, also referred to as angle detuning, as shown in FIG. 4.

Since DE is known, the shape of the theoretical Bragg curve according to Kogelnik is determined only by the thickness d' of the photopolymer layer. Δn is corrected via DE for a given thickness d' so that measurement and theory of DE always agree. d' is now adjusted until the angular positions of the first secondary minima of the theoretical Bragg curve correspond to the angular positions of the first secondary maxima of the transmitted intensity and in addition the full width at half maximum (FWHM) for the theoretical Bragg curve and for the transmitted intensity correspond.

Since the direction in which a reflection hologram rotates on reconstruction by means of an Ω scan, but the detector for the diffracted light can detect only a finite angular range, the Bragg curve of broad holograms (small d') is not completely registered with an Ω scan, but only the central region, with suitable detector positioning. The shape of the transmitted intensity which is complementary to the Bragg curve is therefore additionally used for adjusting the layer thickness d'.

FIG. 4 shows the plot of the Bragg curve η according to the coupled wave theory (dashed line), of the measured diffraction efficiency (solid circles) and of the transmitted power (black solid line) against the angle detuning ΔΩ.

For one formulation, this procedure was possibly repeated several times for different exposure times t on different media in order to determine at which mean energy dose of the incident laser beam during recording of the hologram DE becomes the saturation value. The mean energy dose E is obtained as follows from the powers of the two partial beams coordinated with the angles $\alpha_0$ and $\beta_0$ (reference beam with $P_r$=0.50 mW and signal beam with $P_s$=0.63 mW), the exposure time t and the diameter of the iris diaphragm (0.4 cm):

$$E(mJ/cm^2) = \frac{2 \cdot [P_r + P_s] \cdot t(s)}{\pi \cdot 0.4^2 \text{ cm}^2}$$

The powers of the partial beams were adjusted so that, at the angles $\alpha_0$ and $\beta_0$ used, the same power density is reached in the medium.

As an alternative I, a test equivalent to the setup shown in FIG. 1 was also carried out using a green laser having the emission wavelength λ of 532 nm in vacuo. Here, $\alpha_0$=−11.5° and $\beta_0$=33.5° and $P_r$=1.84 mW and $P_s$=2.16 mW.

As an alternative II, a test equivalent to the setup shown in FIG. 1 was also carried out using a blue laser having the emission wavelength 2 of 473 nm in vacuo. Here, $\alpha_0$ is −22.0° and $\beta_0$ is 42.0° and $P_r$ is 1.78 mW and $P_s$ is 2.22 mW.

In examples, in each case the maximum value in Δn is reported, and the doses used are between 4 and 64 mJ/cm² per arm.

Measurement of the Plateau Modulus $G_0$ of the Photopolymers by Means of an Oscillation Rheometer in the Present Invention The still liquid formulation having the composition described below is introduced into the plate-plate measuring system of a rheometer (from Anton Paar Physica Model MCR 301, equipped with the oven model CTD 450 which was preheated to 50° C.). The curing of the matrix of the photopolymer formulation over the time is then measured under the following conditions:

Plate spacing 250 μm.
Oscillation measuring mode at a constant angular frequency $\omega_0$ of 10 rad/s and a regulated deformation amplitude of 1%.
Temperature 50° C., normal force regulation set at 0 Newton
Recording of the storage modulus G' over the measuring time up to a constant value $G_{max}$ of G' was reached or for not more than 3 hours.

Figure 2:
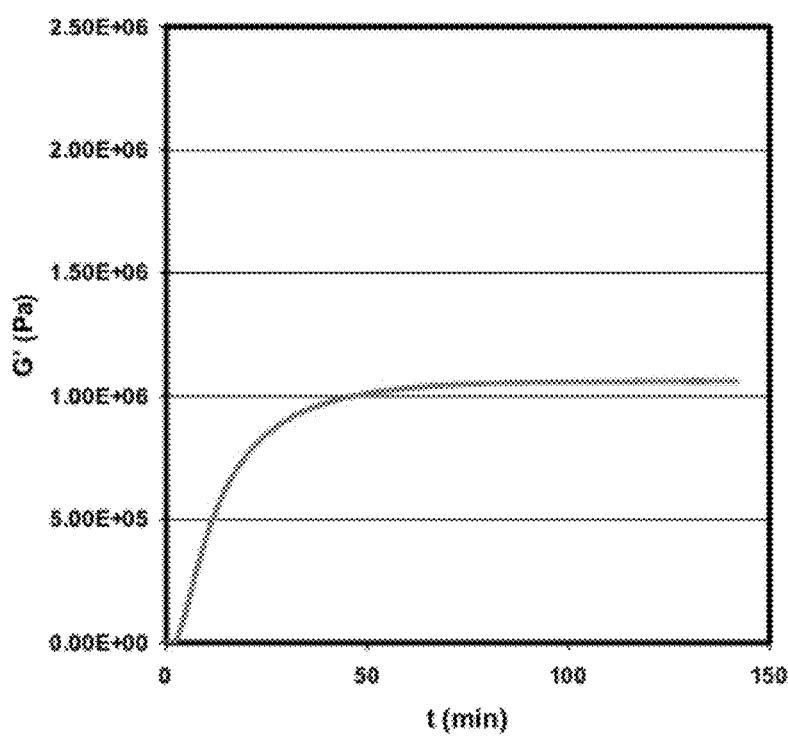
FIG. 2 illustrates a graph showing the variation of the curing of the matrix network (left) and testing for plateau behaviour (G' independently of ω) (right)

This value of the modulus is taken as the plateau modulus $G_0$ to be determined Examples of typical measured curves are to be found in FIG. 2.

FIG. 2 shows the variation of the curing of the matrix network (left) and testing for plateau behaviour (G' independently of ω) (right).

Measurement of the Layer Thickness of the Photopolymer Layers

The physical layer thickness was determined using commercially available white light interferometers, such as, for example, the device FTM-Lite NIR layer thickness gauge from Ingenieursbüro Fuchs.

The determination of the layer thickness is based in principle on interference phenomena on thin layers. Light waves which have been reflected by two interfaces of different optical density are superposed to one another. The undisturbed superposition of the reflected partial beams now leads to periodic brightening and extinction in the spectrum of a white continuum radiator (e.g. halogen lamp). This superposition is referred to as interference by the person skilled in the art. These interference spectra are measured and mathematically evaluated.

Starting Materials
Isocyanates Used (Components A)
Isocyanate component 1 (component a1) is an experimental product of Bayer MaterialScience AG, Leverkusen, Germany, hexane diisocyanate-based polyisocyanate, proportion of iminooxadiazinedione at least 30%, NCO content: 23.5%.

Isocyanate component 2 (component a2) is an experimental product of Bayer MaterialScience AG, Leverkusen, Germany, aliphatic polyisocyanate based on hexane diisocyanate, NCO content about 20%.

Isocyanate component 3 (component a3) is an experimental product of Bayer MaterialScience AG, Leverkusen, Germany, full allophanate of hexane diisocyanate on polypropylene glycol having a number average molar mass of about 280 g/mol, NCO content: 16.5-17.3%.

Isocyanate component 4 (component a4) is a commercially available product of Bayer MaterialScience AG, Leverkusen, Germany, mixture of 29.4 mol % of isocyanurate based on HDI with 70.6 mol % of the urethane of poly($\epsilon$-caprolactone) having a number average molar mass of 650 g/mol with HDI, NCO content 10.5-11.5%.

Isocyanate component 5 (component a5) is a commercially available product of Bayer MaterialScience AG, Leverkusen, Germany, aliphatic biuret type based on hexamethylene diisocyanate, NCO content: 22.5-23.5%.

Isocyanate-Reactive Components Used (Component B)

Polyol 1 (component b1) is an experimental product of Bayer MaterialScience AG, Leverkusen, Germany; the preparation is described below.

Polyol 2 (component b2) is an experimental product of Bayer MaterialScience AG, Leverkusen, Germany; the preparation is described below.

Polyol 3 (component b3) is an experimental product of Bayer MaterialScience AG, Leverkusen, Germany; the preparation is described below.

Polyol 4 (component b4) is an experimental product of Bayer MaterialScience AG, Leverkusen, Germany; the preparation is described below.

Radiation-Curing Compound Used (Component B)

Acrylate 1 (component B1) is an experimental product of Bayer MaterialScience AG, Leverkusen, Germany, the preparation is described below.

Acrylate 2 (component B2) is an experimental product of Bayer MaterialScience AG, Leverkusen, Germany, the preparation is described below.

Isocyanate component 1 has the Bayer trade name Desmodur® N 3900.

Acrylate 3 (component B3) is an experimental product of Bayer MaterialScience AG, Leverkusen, Germany, the preparation is described below.

Isocyanate component 2 has the Bayer trade name Desmodur® XP 2580

Components of the Photoinitiator Systems Used (Component C)

Coinitiator 1 tetrabutylammonium tris(3-chloro-4-methylphenyl)(hexyl)borate, [1147315-11-4] is an experimental product produced by Ciba Inc., Basel, Switzerland.

Isocyanate component 3 has the Bayer trade name Desmodur® XP 2747

Dye 1 is new methylene blue (CAS 1934-16-3) and was obtained from SIGMA-ALDRICH CHEMIE GmbH, Steinheim, Germany.

Dye 2 is safranine O (CAS 477-73-6) and was obtained from SIGMA-ALDRICH CHEMIE GmbH, Steinheim, Germany.

Isocyanate component 4 has the Bayer trade name Desmodur® N 3800

Dye 3 is ethyl violet (CAS 2390-59-2) and was obtained in 80% purity from SIGMA-ALDRICH CHEMIE GmbH, Steinheim, Germany, and used in this form.

Dye 4 is astrazone orange G (CAS 3056-93-7) and was obtained from SIGMA-ALDRICH CHEMIE GmbH, Steinheim, Germany.

Isocyanate component 5 has the Bayer trade name Desmodur® N 3200

Non-Photopolymerizable Components Used (Component D)

The non-photopolymerizable components (component D1 to D10) are experimental products of Bayer MaterialScience AG, Leverkusen, Germany, the preparation of which is described below.

Catalyst Used (Component E)

Catalyst 1 (component E1): Urethanization catalyst, dimethylbis[(1-oxoneodecyl)oxy]stannane, commercially available product of Momentive Performance Chemicals, Wilton, Conn., USA (used as 10% strength solution in N-ethylpyrrolidone).

Auxiliaries and Additives Used (Component E)

BYK® 310: Silicone-based surface additive of BYK-Chemie GmbH, Wesel, Germany (component G1) (25% strength solution in xylene)

Desmorapid® Z (dibutyltin dilaurate) is a urethanization catalyst and commercially available product of Bayer MaterialScience AG, Leverkusen, Germany DMC catalyst: double metal cyanide catalyst based on zinc hexacyanocobaltate (III), obtainable by the process described in EP-A 700 949.

Irganox 1076 is octadecyl 3,5-di-(tert)-butyl-4-hydroxyhydrocinnamate (CAS 2082-79-3).

Preparation of the Components

Preparation of Polyol 1 (Component B1):

3.621 kg of a difunctional polytetrahydrofuran polyether polyol (equivalent weight 500 g/mol OH) were weighed into a 20 l reaction vessel equipped with a stirrer and 525 mg of DMC catalyst were added. Heating was then effected to 105° C. while stirring at about 70 rpm. By applying a vacuum and depressurizing with nitrogen three times, air was exchanged for nitrogen. After the stirrer speed had been increased to 300 rpm, nitrogen was passed through the mixture from below for 54 minutes with the vacuum pump running and at a pressure of about 0.1 bar. Thereafter, a pressure of 0.2 bar was established by means of nitrogen and 363 g of propylene oxide (PO) were passed in to initiate polymerization. As a result, the pressure increased to 2.42 bar. After 7 minutes, the pressure had fallen again to 0.34 bar and a further 11.379 kg of PO were metered in at 2.9 bar over a period of 2 h 29 min. 47 minutes after the end of the PO metering, a vacuum was applied at a residual pressure of 1.9 bar and complete degassing was effected. The product was stabilized by addition of 7.5 g of Irganox 1076 and obtained as a colourless, viscous liquid (OH number: 27.6 mg KOH/g, viscosity at 25° C.: 1498 mPas).

Preparation of Polyol 2 (Component B2):

2475 g of a difunctional polytetrahydrofuran polyether polyol (equivalent weight 325 g/mol OH) were weighed into a 20 l reaction vessel equipped with a stirrer and 452.6 mg of DMC catalyst were added. Heating to 105° C. was then effected while stirring at about 70 rpm. By applying a vacuum and depressurizing with nitrogen three times, air was exchanged for nitrogen. After the stirrer speed had been increased to 300 rpm, nitrogen was passed through the mixture from below for 57 minutes with the vacuum pump running and at a pressure of about 0.1 bar. Thereafter, a pressure of 0.5 bar was established by means of nitrogen and 100 g of ethylene oxide (EO) and 150 g of PO were passed in simultaneously to initiate the polymerization. As a result, the pressure increased to 2.07 bar. After 10 minutes, the pressure had fallen again to 0.68 bar and a further 5.116 kg of EO and 7.558 kg of PO as a mixture were passed in at 2.34 bar over a period of 1 h 53 min. 31 min after the end of the epoxide metering, a vacuum was provided at a residual pressure of 2.16 bar and complete degassing was effected. The product was stabilized by addition of 7.5 g of Irganox 1076 and was obtained as slightly turbid, viscous liquid (OH number 27.1 mg KOH/g, viscosity at 25° C.: 1636 mPas).

Preparation of Polyol 3 (Component B3):

0.18 g of tin octoate, 374.8 g of ε-caprolactone and 374.8 g of a difunctional polytetrahydrofuran polyether polyol (equivalent weight 500 g/mol OH) were initially introduced into a 1 l flask and heated to 120° C. and kept at this temperature until the solids content (proportion of the non-volatile constituents) was 99.5% by weight or higher. Thereafter, cooling was effected and the product was obtained as a waxy solid.

Preparation of Polyol 4 (Component B4):

2465 g of a difunctional polytetrahydrofuran polyether polyol (equivalent weight 325 g/mol OH) were weighed into a 20 l reaction vessel equipped with a stirrer and 450.5 mg of DMC catalyst were added. Heating to 105° C. was then effected while stirring at about 70 rpm. By applying a vacuum and depressurizing with nitrogen three times, air was exchanged for nitrogen. After the stirrer speed had been increased to 300 rpm, nitrogen was passed through the mixture from below for 72 minutes with the vacuum pump running and at a pressure of about 0.1 bar. Thereafter, a pressure of 0.3 bar was established by means of nitrogen and 242 g of propylene oxide (PO) were passed in to initiate the polymerization. As a result, the pressure increased to 2.03 bar. After 8 minutes, the pressure had fallen again to 0.5 bar and a further 12.538 kg of PO were metered in at 2.34 bar over a period of 2 h 11 min. 17 minutes after the end of the PO metering, a vacuum was applied at a residual pressure of 1.29 bar and complete degassing was effected. The product was stabilized by addition of 7.5 g of Irganox 1076 and obtained as a colourless, viscous liquid (OH number: 27.8 mg KOH/g, viscosity at 25° C.: 1165 mPas).

Preparation of Acrylate 1 (Component B1) (phosphorothioyl-tris(oxy-4,1-phenyleneiminocarbonyloxyethane-2,1-diyl) triacrylate):

0.1 g of 2,6-di-tert-butyl-4-methylphenol, 0.05 g of dibutyltin dilaurate (Desmorapid® Z, Bayer MaterialScience AG, Leverkusen, Germany) and 213.07 g of a 27% strength solution of tris(p-isocyanatophenyl) thiophosphate in ethyl acetate (Desmodur® RFE, product of Bayer MaterialScience AG, Leverkusen, Germany) were initially taken in a 500 ml round-bottomed flask and heated to 60° C. Thereafter, 42.37 g of 2-hydroxyethyl acrylate were added dropwise and the mixture was further kept at 60° C. until the isocyanate content had fallen below 0.1%. Thereafter, cooling was effected and the ethyl acetate was completely removed in vacuo. The product was obtained as a semicrystalline solid.

Preparation of Acrylate 2 (Component B2) 2-({[3-(methylsulphanyl)phenyl]carbamoyl}oxy)ethyl prop-2-enoate):

0.02 g of 2,6-di-tert-butyl-4-methylphenol, 0.01 g of Desmorapid® Z, 11.7 g of 3-(methylthio)phenyl isocyanate were initially introduced and initially introduced into a 100 ml round-bottomed flask and heated to 60° C. Thereafter, 8.2 g of 2-hydroxyethyl acrylate were added dropwise and the mixture was further kept at 60° C. until the isocyanate content had fallen below 0.1%. Cooling was then effected. The product was obtained as a light yellow liquid.

Preparation of Acrylate 3 (Component B3) (mixture of (4-methylbenzene-1,3-diyl)bis[carbamoyloxy-3-(biphenyl-2-yloxy)propane-2,1-diyl] bisacrylate and (4-methylbenzene-1,3-diyl)bis[carbamoyloxy-3-(biphenyl-2-yloxy)propane-1,2-diyl] bisacrylate and analogous isomers):

430.2 g of Denacol EX 142 (Nagase-Chemtex, Japan), 129.7 g of acrylic acid, 1.18 g of triphenylphosphine and 0.0056 g of 2,6-di-tert-butyl-4-methylphenol were initially introduced into a three-necked flask having a reflux condenser and stirrer. Air was slowly passed through the mixture and the latter was thermostated at 60° C. Stirring is then effected for 24 hours at 90° C. A clear liquid having an OH number of 157.8 mg KOH/g was obtained. 21.3 g of this intermediate product and 5.2 g of a mixture of 2,4- and 2,6-toluidene diisocyanate (Desmodur T80, Bayer MaterialScience AG, Leverkusen, Germany) were initially introduced into a three-necked flask having a reflux condenser and stirrer. Air was slowly passed through the mixture and the latter was thermostated at 60° C. After an initial exothermic reaction, the product was stirred for 24 hours at 60° C. A clear, colourless, glassy product having NCO of 0% was obtained.

Preparation of Photoinitiator System 1 (Component C1)

In the dark or under suitable lighting, 0.05 g of dye 1, 0.05 g of dye 2, 0.05 g of dye 4, 1.50 g of coinitiator 1 are dissolved in 3.50 g of N-ethylpyrrolidone in a beaker. The corresponding percentages by weight of this solution are used for preparing the example media.

Preparation of Photoinitiator System 2 (Component C2)

In the dark or under suitable lighting, 0.05 g of dye 1, 0.05 g of dye 3, 0.05 g of dye 4, 1.50 g of coinitiator 1 are dissolved in 3.50 g of N-ethylpyrrolidone in a beaker. The corresponding percentages by weight of this solution are used for preparing the example media.

Preparation of Photoinitiator System 3 (Component C3)

In the dark or under suitable lighting, 0.10 g of dye 1, 1.00 g of coinitiator 1 are dissolved in 3.50 g of N-ethylpyrrolidone in a beaker. The corresponding percentages by weight of this solution are used for preparing the example media.

Preparation of the Non-Photopolymerizable Component (Component D1) (bis(2,2,3,3,4,4,5,5,6,6,7,7-dodecafluoroheptyl)-(2,2,4-trimethylhexane-1,6-diyl) biscarbamate):

0.02 g of dibutyltin dilaurate (Desmorapid Z, Bayer MaterialScience AG, Leverkusen, Germany) and 3.6 g of 2,4,4-trimethylhexane 1,6-diisocyanate (TMDI) were initially introduced into a 50 ml round-bottomed flask and heated to 60° C. Thereafter, 11.9 g of 2,2,3,3,4,4,5,5,6,6,7,7-dodecafluoroheptan-1-ol were added dropwise and the mixture was further kept at 60° C. until the isocyanate content had fallen below 0.1%. Cooling was then effected. The product was obtained as a colourless oil.

The additives described below in Table 1 (component D2 to D10) were prepared in a manner analogous to that described for the additive (component D1) in the stated compositions.

| Additive | Name | Isocyanate and amount | Alcohol and amount | Catalyst and amount | Temp [° C.] | Description |
|---|---|---|---|---|---|---|
| D2 | 2,2,3,3,4,4,5,5,6,6,7,7,8,8,9,9-Hexadecafluorononyl butylcarbamate | n-Butyl isocyanate 186 g | 2,2,3,3,4,4,5,5,6,6,7,7,8,8,9,9-Hexadecafluorononanol 813 g | Desmorapid Z 0.50 g | 60° C. | colourless liquid |
| D3 | 2,2,2-Trifluoroethyl hexylcarbamate | n-Hexyl isocyanate 55.9 g | Trifluoroethanol 44.0 g | Desmorapid Z 0.05 g | 60° C. | colourless liquid |

-continued

| Additive | Name | Isocyanate and amount | Alcohol and amount | Catalyst and amount | Temp [° C.] | Description |
|---|---|---|---|---|---|---|
| D4 | Bis(1,1,1,3,3,3-hexafluoropropan-2-yl)-(2,2,4-trimethylhexane-1,6-diyl) biscarbamate | 2,4,4-Trimethylhexane 1,6-diisocyanate (TMDI) 50.0 g | Hexafluoro-2-propanol 80.0 g | Desmorapid Z 0.07 g | 60° C. | colourless liquid |
| D5 | 2,2,3,3,4,4,5,5,6,6,7,7-Dodecafluoroheptyl butylcarbamate | n-Butyl isocyanate 3.44 g | 2,2,3,3,4,4,5,5,6,6,7,7-Dodecafluoroheptan-1-ol 11.54 g | Desmorapid Z 0.02 g | 70° C. | colourless liquid |
| D6 | 2,2,3,3,4,4,5,5,6,6,7,7-Dodecafluoroheptyl hexylcarbamate | n-Hexyl isocyanate 4.15 g | 2,2,3,3,4,4,5,5,6,6,7,7-Dodecafluoroheptan-1-ol 10.84 g | Desmorapid Z 0.02 g | 70° C. | colourless liquid |
| D7 | 2,2,3,3,4,4,5,5,6,6,7,7-Dodecafluoroheptyl propan-2-ylcarbamate | i-Propyl isocyanate 3.06 g | 2,2,3,3,4,4,5,5,6,6,7,7-Dodecafluoroheptan-1-ol 11.93 g | Desmorapid Z 0.02 g | 70° C. | colourless liquid |
| D8 | 2,2,3,3,4,4,4-Heptafluorobutyl hexylcarbamate | n-Hexyl isocyanate 5.82 g | 2,2,3,3,4,4,4-Heptafluorobutan-1-ol 9.16 g | Desmorapid Z 0.02 g | 70° C. | colourless liquid |
| D9 | 2,2,3,3,4,4,5,5,6,6,7,7,8,8,9,9-Hexadecafluorononyl hexylcarbamate | n-Hexyl isocyanate 3.40 g | 2,2,3,3,4,4,5,5,6,6,7,7,8,8,9,9-Hexadecafluorononan-1-ol 11.6 g | Desmorapid Z 0.02 g | 70° C. | colourless solid |
| D10 | 2,2,3,3,4,4,5,5,6,6,7,7,8,8,9,9-Hexadecafluorononyl cyclohexylcarbamate | Cyclohexyl isocyanate 3.37 g | 2,2,3,3,4,4,5,5,6,6,7,7,8,8,9,9-Hexadecafluorononan-1-ol 11.61 g | Desmorapid Z 0.02 g | 70° C. | colourless solid |

Preparation of the Samples and Example Media
Preparation of the Photopolymer Formulation (F) without Photoinitiator C) for Determining the Plateau Modulus $G_0$ of the Photopolymers.

For the preparation of the photopolymer formulation for determining the modulus $G_0$, the various writing monomers (components B) and optionally additives (parts of component E) are dissolved in the isocyanate-reactive component b) (as part of component A), optionally at 60° C. Optionally, heating to 60° C. is effected for not more than 10 minutes in a drying oven. Thereafter, isocyanate component a) (other part of component A) is added and mixing is effected in the Speedmixer for 1 minute. Subsequently, a solution of component E1) in butyl acetate is added and mixing is effected in the Speedmixer again for 1 minute (further parts of component E). The concentration of component E1) in butyl acetate is 10% by weight. The amounts of this solution which are described in Table 2 were used.

Table 2 lists the investigated examples of the photopolymer formulations without photoinitiator system C) for determining the plateau modulus $G_0$ of the photopolymers, which examples are prepared in this manner.

TABLE 2

Photopolymer formulations which were investigated with regard to their modulus $G_0$ of the photopolymers

| Photopolymer formulation without initiator | Comparison with film medium | Isocyanate component | Proportion (g) | Isocyanate-reactive component | Proportion (g) | NCO:OH | Photopolymerizable monomer 1 |
|---|---|---|---|---|---|---|---|
| F1 | M4 | a1 | 0.366 | b1 | 4.121 | 1.02:1 | B1 |
| F2 | M5 | a2 | 0.573 | b4 | 5.414 | 1.02:1 | B1 |
| F3 | M9 | a1 | 0.706 | b3 | 3.781 | 1.02:1 | B1 |
| F4 | M13 | a3 | 0.496 | b4 | 3.991 | 1.02:1 | B1 |
| F5 | M14 | a3 | 0.534 | b2 | 3.950 | 1.02:1 | B1 |
| F6 | M15 | a3 | 0.534 | b2 | 3.950 | 1.02:1 | B1 |
| F7 | M16 | a4 | 0.757 | b2 | 3.730 | 1.02:1 | B1 |
| F8 | M17 | a4 | 0.757 | b2 | 3.730 | 1.02:1 | B1 |
| F9 | M18 | a5 | 0.370 | b2 | 4.117 | 1.02:1 | B1 |
| F10 | M23 | a1 | 0.706 | b3 | 3.781 | 1.02:1 | B3 |
| F11 | M24 | a3 | 0.534 | b2 | 3.950 | 1.02:1 | B3 |

| Photopolymer formulation without initiator | Proportion (% by weight) | Photopolymerizable monomer 2 | Proportion (% by weight) | Non-photopolymerizable component | Proportion (% by weight) | Catalyst in solution (butyl acetate) | Proportion (g) |
|---|---|---|---|---|---|---|---|
| F1 | 15.0 | B2 | 15.0 | D1 | 25.0 | E1 | 0.0300 |
| F2 | 20.0 | B2 | 20.0 | | | E1 | 0.0300 |
| F3 | 15.0 | B2 | 15.0 | D1 | 25.0 | E1 | 0.0300 |
| F4 | 15.0 | B2 | 15.0 | D2 | 25.0 | E1 | 0.0300 |
| F5 | 15.0 | B2 | 15.0 | D1 | 25.0 | E1 | 0.0300 |
| F6 | 15.0 | B2 | 15.0 | D2 | 25.0 | E1 | 0.0300 |
| F7 | 15.0 | B2 | 15.0 | D1 | 25.0 | E1 | 0.0300 |
| F8 | 25.0 | B2 | 15.0 | D1 | 15.0 | E1 | 0.0300 |
| F9 | 25.0 | B2 | 15.0 | D1 | 15.0 | E1 | 0.0300 |
| F10 | 15.0 | B2 | 15.0 | D1 | 25.0 | E1 | 0.0300 |
| F11 | 15.0 | B2 | 15.0 | D1 | 25.0 | E1 | 0.0300 |

Table 3 lists the investigated examples of the photopolymer formulations which are used for the continuous preparation of holographic films with regard to their composition.

For the preparation of the photopolymer formulation, the photopolymerizable monomers (component B), the nonpolymerizable components D, then Fomrez® UL 28 (component E1) and the surface-active additives BYK® 310 (component E2) are added stepwise to the components polyol (component b) and mixed. Thereafter, a solution of the component C of the photopolymer solution is added in the dark and mixed so that a clear solution was obtained. Optionally, the formulation can be heated at 60° C. for a short time in order to promote the solubility of the starting materials. Finally, the corresponding isocyanate component a is added at 30° C. and mixing is effected again. The liquid material obtained is then applied by means of a knife coater or slot die to a 36 µm thick polyethylene terephthalate film and dried for 4.5 minutes at the corresponding drying temperature (cf. example Table 6) in an air-circulation dryer. The photopolymer layer is then covered with a 40 µm thick polyethylene film and is rolled up.

The desired target layer thickness of the dried photopolymers are preferably between 10 and 20 µm. The layer thicknesses achieved for the holographic films produced are shown in Table 6.

The production speeds are preferably in the range from 0.2 m/min to 300 m/min and particularly preferably in the range from 1.0 m/min to 50 m/min.

This type of holographic films is particularly suitable for determining the performance thereof according to the methods described in the section Measurement of the holographic properties DE and Δn of the holographic media by means of two-beam interference in a reflection arrangement.

TABLE 3

Holographic media which were tested with regard to their performance Δn

| Holographic medium | Isocyanate component | Proportion (% by weight) | Isocyanate-reactive component | Proportion (% by weight) | NCO:OH | Photo-polymerizable monomer1 | Proportion (% by weight) | Photo-polymerizable monomer 2 | Proportion (% by weight) |
|---|---|---|---|---|---|---|---|---|---|
| M1  | a1 | 6.30 | b3 | 33.80 | 1.02:1 | B1 | 20.0 | B2 | 20.0 |
| M2  | a1 | 6.30 | b3 | 33.80 | 1.02:1 | B1 | 20.0 | B2 | 20.0 |
| M3  | a1 | 6.30 | b3 | 33.80 | 1.02:1 | B1 | 20.0 | B2 | 20.0 |
| M4  | a1 | 3.23 | b1 | 36.07 | 1.02:1 | B1 | 15.0 | B2 | 15.0 |
| M5  | a2 | 5.27 | b4 | 49.23 | 1.02:1 | B1 | 20.0 | B2 | 20.0 |
| M6  | a1 | 6.30 | b3 | 33.80 | 1.02:1 | B1 | 20.0 | B2 | 20.0 |
| M7  | a3 | 4.40 | b2 | 34.85 | 1.02:1 | B1 | 15.0 | B2 | 15.0 |
| M8  | a1 | 6.16 | b3 | 33.23 | 1.02:1 | B1 | 15.0 | B2 | 15.0 |
| M9  | a1 | 6.16 | b3 | 33.23 | 1.02:1 | B1 | 15.0 | B2 | 15.0 |
| M10 | a1 | 6.30 | b3 | 33.80 | 1.02:1 | B1 | 20.0 | B2 | 20.0 |
| M11 | a1 | 6.30 | b3 | 33.80 | 1.02:1 | B1 | 20.0 | B2 | 20.0 |
| M12 | a1 | 6.30 | b3 | 33.80 | 1.02:1 | B1 | 20.0 | B2 | 20.0 |
| M13 | a3 | 4.52 | b4 | 34.93 | 1.02:1 | B1 | 15.0 | B2 | 15.0 |
| M14 | a3 | 4.52 | b4 | 34.93 | 1.02:1 | B1 | 15.0 | B2 | 15.0 |
| M15 | a3 | 4.70 | b2 | 34.75 | 1.02:1 | B1 | 15.0 | B2 | 15.0 |
| M16 | a4 | 6.93 | b2 | 32.27 | 1.02:1 | B1 | 15.0 | B2 | 15.0 |
| M17 | a4 | 6.95 | b2 | 32.35 | 1.02:1 | B1 | 25.0 | B2 | 15.0 |
| M18 | a5 | 3.42 | b2 | 35.88 | 1.02:1 | B1 | 25.0 | B2 | 15.0 |
| M19 | a1 | 6.30 | b3 | 33.80 | 1.02:1 | B1 | 20.0 | B2 | 20.0 |
| M20 | a3 | 4.40 | b2 | 34.85 | 1.02:1 | B1 | 15.0 | B2 | 15.0 |
| M21 | a3 | 4.40 | b2 | 34.85 | 1.02:1 | B1 | 15.0 | B2 | 15.0 |
| M22 | a3 | 4.40 | b2 | 34.85 | 1.02:1 | B1 | 15.0 | B2 | 15.0 |
| M23 | a1 | 6.16 | b3 | 33.23 | 1.02:1 | B3 | 15.0 | B2 | 15.0 |
| M24 | a3 | 4.40 | b2 | 34.85 | 1.02:1 | B3 | 15.0 | B2 | 15.0 |
| M25 | a4 | 6.60 | b2 | 32.65 | 1.02:1 | B3 | 15.0 | B2 | 15.0 |

| Holographic medium | Non-photo-polymerizable component | Proportion (% by weight) | Photo-initiator | Proportion (% by weight) | Auxiliaries and additives | Proportion (% by weight) | Catalyst in solution | Proportion (% by weight) |
|---|---|---|---|---|---|---|---|---|
| M1  | D3  | 15.0 | C3 | 4.59 | E2 | 0.30 | E1 | 0.010 |
| M2  | D7  | 15.0 | C3 | 4.59 | E2 | 0.30 | E1 | 0.010 |
| M3  | D8  | 15.0 | C3 | 4.59 | E2 | 0.30 | E1 | 0.010 |
| M4  | D1  | 25.0 | C2 | 5.30 | E2 | 0.30 | E1 | 0.100 |
| M5  | —   | —    | C1 | 5.15 | E2 | 0.30 | E1 | 0.050 |
| M6  | D2  | 15.0 | C3 | 4.59 | E2 | 0.30 | E1 | 0.010 |
| M7  | D8  | 25.0 | C2 | 5.40 | E2 | 0.30 | E1 | 0.050 |
| M8  | D2  | 25.0 | C1 | 5.30 | E2 | 0.30 | E1 | 0.010 |
| M9  | D1  | 25.0 | C1 | 5.30 | E2 | 0.30 | E1 | 0.010 |
| M10 | D2  | 15.0 | C3 | 4.59 | E2 | 0.30 | E1 | 0.010 |
| M11 | D6  | 15.0 | C3 | 4.59 | E2 | 0.30 | E1 | 0.010 |
| M12 | D10 | 15.0 | C3 | 4.59 | E2 | 0.30 | E1 | 0.010 |
| M13 | D2  | 25.0 | C1 | 5.15 | E2 | 0.30 | E1 | 0.100 |
| M14 | D1  | 25.0 | C1 | 5.15 | E2 | 0.30 | E1 | 0.100 |
| M15 | D2  | 25.0 | C1 | 5.15 | E2 | 0.30 | E1 | 0.100 |
| M16 | D1  | 25.0 | C2 | 5.40 | E2 | 0.30 | E1 | 0.100 |
| M17 | D1  | 15.0 | C2 | 5.30 | E2 | 0.30 | E1 | 0.100 |
| M18 | D1  | 15.0 | C2 | 5.30 | E2 | 0.30 | E1 | 0.100 |
| M19 | D1  | 15.0 | C3 | 4.59 | E2 | 0.30 | E1 | 0.010 |
| M20 | D9  | 25.0 | C2 | 5.40 | E2 | 0.30 | E1 | 0.050 |

TABLE 3-continued

| Holographic media which were tested with regard to their performance Δn | | | | | | | | |
|---|---|---|---|---|---|---|---|---|
| M21 | D4 | 25.0 | C2 | 5.40 | E2 | 0.30 | E1 | 0.050 |
| M22 | D5 | 25.0 | C2 | 5.40 | E2 | 0.30 | E1 | 0.050 |
| M23 | D1 | 25.0 | C1 | 5.30 | E2 | 0.30 | E1 | 0.010 |
| M24 | D1 | 25.0 | C2 | 5.40 | E2 | 0.30 | E1 | 0.050 |
| M25 | D1 | 25.0 | C2 | 5.40 | E2 | 0.30 | E1 | 0.050 |

Results of Modulus $G_0$ in Comparison to Rollability

The following measured values for $G_0$ (Pa) and the quality of the rollability were obtained and are shown in Table 4:

TABLE 4

Holographic media which were tested with regard to modulus $G_0$

| Photopolymer formulation without initiator | Holographic medium | Example type | Proportion by weight (%) of components C, based on the total formulation | $G_0$ in Pa | Rollability |
|---|---|---|---|---|---|
| F1 | M4 | Comparative Example 4 | 30.0 | 25 000 | − |
| F2 | M5 | Comparative Example 5 | 40.0 | 7000 | −− |
| F3 | M9 | Example 2 | 30.0 | 489 000 | ++ |
| F4 | M13 | Example 6 | 30.0 | 31 000 | + |
| F5 | M14 | Example 7 | 30.0 | 90 000 | + |
| F6 | M15 | Example 8 | 30.0 | 85 000 | + |
| F7 | M16 | Example 9 | 30.0 | 52 000 | + |
| F8 | M17 | Example 10 | 40.0 | 49 000 | + |
| F9 | M18 | Example 11 | 40.0 | 34 000 | + |
| F10 | M23 | Example 16 | 30.0 | 242 000 | ++ |
| F11 | M24 | Example 17 | 30.0 | 44 000 | + |

Good blockability and rollability are obtained at values of $G_0 > 0.03$ MPa. $G_0$ should preferably be >0.05 MPa and very particularly preferably >0.1 MPa.

For evaluating the rollability, two features are to be assessed in the finished product. Firstly, the homogeneity of the photopolymer layer thickness is visually rated. The edge regions of the photopolymer in the running direction of the web are particularly striking here and to be rated as good. Mostly slight unevenness in the layer thicknesses due to the colouring of the photopolymer can be observed here, which may result from a shift of material on application of pressure through the protective film.

As further aspect, the tack of the photopolymer layer is rated. In the case of this rating, the protective film is peeled off the photopolymer. During the process, the tack can be empirically determined via the applied force for peeling off and the observation of the interface between photopolymer and protective film. Here, the possible destruction of the photopolymer during peeling is a particularly strong indication of very good adhesion between photopolymer and protective film, which in turn is brought about by too low a blocking resistance of the polymer.

The ratings of the individual qualities of the rollability are explained below:
++ no shift of the layer thicknesses, very easy detachment of the protective film without disturbances in the film
+ no shift of the layer thicknesses, easy detachment of the protective film without disturbances in the film
− slight layer thickness variation in the edge region, the protective film is difficult to peel off without destroying the surface
−− significant layer thickness variations in the edge region, severe "fraying" of the coating edge, the protective film is difficult to peel off and disturbances occur in the photopolymer TGA 95 Results The following TGA 95 measured values were determined for the writing monomers B) according to the formulae II and III described non-photopolymerizable components D):

TABLE 5

List of components B and D which were tested with regard to TGA 95

| Component | Designation | TGA 95 in ° C. |
|---|---|---|
| B1 | Phosphorothioyltris(oxy-4,1-phenyleneimino-carbonyloxyethane-2,1-diyl) triacrylate | 177.2 |
| B2 | 2-({[3-(Methylsulphanyl)phenyl]carbamoyl}oxy)ethyl prop-2-enoate | 190.3 |
| B3 | Mixture of (4-methylbenzene-1,3-diyl)bis[carbamoyloxy-3-(biphenyl-2-yloxy)propane-2,1-diyl] bisacrylate and (4-methylbenzene-1,3-diyl)bis[carbamoyloxy-3-(biphenyl-2-yloxy)propane-1,2-diyl] bisacrylate and analogous isomers | 239.5 |
| D1 | Bis(2,2,3,3,4,4,5,5,6,6,7,7-dodecafluoroheptyl)-(2,2,4-trimethylhexane-1,6-diyl) biscarbamate | 189.5 |
| D2 | 2,2,3,3,4,4,5,5,6,6,7,7,8,8,9,9-Hexadecafluorononyl butylcarbamate | 111.8 |
| D3 | 2,2,2-Trifluoroethyl hexylcarbamate | 72.5 |
| D4 | Bis(1,1,1,3,3,3-hexafluoropropan-2-yl)-(2,2,4-trimethylhexane-1,6-diyl) biscarbamate | 139.1 |
| D5 | 2,2,3,3,4,4,5,5,6,6,7,7-Dodecafluoroheptyl butylcarbamate | 112.6 |
| D6 | 2,2,3,3,4,4,5,5,6,6,7,7-Dodecafluoroheptyl hexylcarbamate | 117.6 |
| D7 | 2,2,3,3,4,4,5,5,6,6,7,7-Dodecafluoroheptyl propan-2-ylcarbamate | 93.3 |
| D8 | 2,2,3,3,4,4,4-Heptafluorobutyl hexylcarbamate | 82.3 |
| D9 | 2,2,3,3,4,4,5,5,6,6,7,7,8,8,9,9-Hexadecafluorononyl hexylcarbamate | 125.9 |

TABLE 5-continued

List of components B and D which
were tested with regard to TGA 95

| Component | Designation | TGA 95 in ° C. |
|---|---|---|
| D10 | 2,2,3,3,4,4,5,5,6,6,7,7,8,8,9,9-Hexadeca-fluorononyl cyclohexylcarbamate | 130.8 |

Δn Results

The following measured values of the holographic media described in Table 3 are shown in Table 6:

TABLE 6

Holographic measured results Δn as a function of various compositions and drying conditions

| Holographic medium | Example type | Drying (time min/ temperature ° C.) | Dry layer thickness (μm) | Δn (633 nm) | E (mJ/cm$^2$) | Δn (532 nm) | E (mJ/cm$^2$) | Δn (473 nm) | E (mJ/cm$^2$) |
|---|---|---|---|---|---|---|---|---|---|
| M1 | Comparative Example 1 | 4.5/80 | 12-14 | 0.012 | 9-36 | | | | |
| M2 | Comparative Example 2 | 4.5/80 | 15-17 | 0.011 | 9-36 | | | | |
| M3 | Comparative Example 3 | 4.5/80 | 15-16 | 0.011 | 9-36 | | | | |
| M4 | Comparative Example 4 | 4.5/80 | 8-12 | | | 0.033 | 16-128 | | |
| M5 | Comparative Example 5 | 4.5/80 | 29-32 | 0.026 | 9-36 | 0.026 | 16-128 | | |
| M6 | Comparative Example 6 | 4.5/100 | 16-18 | 0.010 | 9-36 | | | | |
| M7 | Comparative Example 7 | 4.5/80 | 15-17 | 0.013 | 9-36 | 0.014 | 16-128 | | |
| M8 | Example 1 | 4.5/80 | 12-14 | 0.037 | 9-36 | 0.034 | 16-128 | | |
| M9 | Example 2 | 4.5/80 | 15-16 | 0.034 | 9-36 | 0.032 | 16-128 | 0.032 | 16-128 |
| M10 | Example 3 | 4.5/80 | 15-16 | 0.038 | 9-36 | | | | |
| M11 | Example 4 | 4.5/80 | 16-17 | 0.027 | 9-36 | | | | |
| M12 | Example 5 | 4.5/80 | 16-17 | 0.029 | 9-36 | | | | |
| M13 | Example 6 | 4.5/80 | 13-14 | | | 0.027 | 16-128 | | |
| M14 | Example 7 | 4.5/80 | 11-12 | | | 0.031 | 16-128 | | |
| M15 | Example 8 | 4.5/80 | 13-16 | 0.033 | 9-36 | 0.028 | 16-128 | | |
| M16 | Example 9 | 4.5/80 | 15-17 | 0.036 | 9-36 | | | | |
| M17 | Example 10 | 4.5/80 | 14-15 | 0.036 | 9-36 | | | | |
| M18 | Example 11 | 4.5/80 | 13-14 | 0.035 | 9-36 | | | | |
| M19 | Example 12 | 4.5/80 | 11-13 | 0.031 | 9-36 | | | | |
| M20 | Example 13 | 4.5/80 | 15-17 | 0.037 | 9-36 | 0.035 | 16-128 | | |
| M21 | Example 14 | 4.5/80 | 15-17 | 0.028 | 9-36 | 0.033 | 16-128 | | |
| M22 | Example 15 | 4.5/80 | 15-17 | 0.029 | 9-36 | 0.030 | 16-128 | | |
| M23 | Example 16 | 4.5/80 | 12-13 | 0.037 | 9-36 | 0.033 | 16-128 | 0.032 | 16-128 |
| M24 | Example 17 | 4.5/80 | 16-17 | 0.034 | 9-36 | | | | |
| M25 | Example 18 | 4.5/80 | 14-15 | 0.033 | 9-36 | | | | |

In particular, Examples M8 to M25 show high Δn values in the film structure.

Owing to a suitable composition of the formulation, experiments M4 and M5 likewise show a good holographic performance. However, the rollability and further processability are nonexistent owing to too low a plateau modulus $G_0$ of <0.030 MPa.

The invention claimed is:

1. A process for producing a holographic film comprising:
  determining the TGA 95 of compounds useful as components for a photopolymer formulation,
  i) providing the photopolymer formulation comprising:
    A) matrix polymers,
    B) writing monomers,
    C) a photoinitiator system,
    D) optionally a non-photopolymerizable component, and
    E) optionally catalysts, free radical stabilizers, solvents, additives and other auxiliaries and/or additives;
  ii) applying the photopolymer formulation as a film to a substrate film; and
  iii) drying the photopolymer formulation on the substrate film at a temperature of between 60 to 120° C.,
  wherein the components chosen for the photopolymer formulation are only compounds having a TGA 95 value greater than 100° C. and at least 30° C. above the drying temperature and wherein the photopolymer formulation has a plateau modulus of greater than or equal to 0.030 MPa,
  wherein the TGA 95 values of the individual photopolymer formulation components are determined by weighing an amount of about 10 mg of a sample of the respective component into a small aluminium pan having a volume of 70 μl, introducing the small aluminium pan an oven of a thermobalance, and measuring the loss of mass of the sample in the open small aluminium pan at a constant oven heating rate of 20 K/min, the start temperature of the oven being 30° C. and the end temperature 600° C., the oven being flushed with a 200 ml/min nitrogen stream during the determination and the temperature at which a loss of mass of the sample of 5% by weight, based on the originally weighed in amount of the sample, has occurred being determined as the TGA 95 value of the respective component.

2. The process according to claim 1, wherein the photopolymer formulation is dried at a temperature of between 70 to 100° C.

3. The process according to claim 1, wherein the photopolymer formulation has a plateau modulus of from 0.03 to 1 MPa.

4. The process according to claim 1, wherein the process further comprises applying a laminating film to the film after the drying in step iii).

5. The process according to claim 4, wherein the film is rolled up together with the laminating film.

6. The process according to claim 1, wherein the matrix polymers comprise polyurethanes.

7. The process according to claim 6, wherein the polyurethanes are obtained by reacting an isocyanate component a) and an isocyanate-reactive component b).

8. The process according to claim 7, wherein the process further comprises:
   I. transporting and metering firstly component a), optionally mixed with one or more of the components B), C), D) and E), and secondly, separately therefrom, transporting and metering component b), optionally mixed with one or more of the components B), C), D) and E)
   II. devolatilizing the streams transported, metered and optionally premixed according to I)
   III. filtering the mixture obtained according to II)
   IV. homogenizing the mixture obtained according to III)
   V. unwinding and pre-treating the substrate material
   VI. coating the substrate material with the mixture obtained according to step IV)
   VII. drying the film coated according to VI)
   VIII. laminating the coated film obtained according to VII)
   IX. winding up of the laminated film obtained according to VIII).

9. The process according to claim 1, wherein the writing monomers comprise acrylates and/or meth(acrylates).

10. The process according to claim 1, wherein the writing monomers comprise a combination of a monofunctional and a polyfunctional writing monomer.

11. The process according to claim 10, wherein the monofunctional writing monomer has the formula (II)

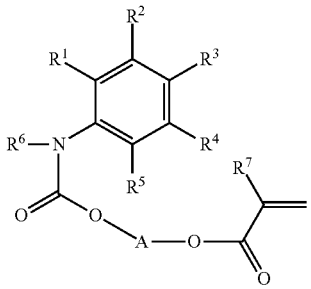

(II)

wherein
R1, R2, R3, R4, R5, in each case independently of one another, represent a hydrogen or halogen atom or a C1-C6-alkyl, trifluoromethyl, C1-C6-alkylthio, C1-C6-alkylseleno, C1-C6-alkyltelluro or nitro group, with the proviso that at least one substituent of the group R1, R2, R3, R4, R5 is not hydrogen,
R6, R7, in each case independently of one another, represent hydrogen or a C1-C6-alkyl group, and
A represents a saturated or unsaturated or linear or branched C1-C6-alkyl radical or a polyethylene oxide radical or a polypropylene oxide radical having in each case 2-6 repeating units in the polymer chain.

12. The process according to claim 11, wherein the monofunctional writing monomer has a glass transition temperature of less than 0° C. and a refractive index of greater than 1.50 at 405 nm.

13. The process according to claim 1, wherein the photopolymer formulation comprises, as an additive, urethanes of the formula (V)

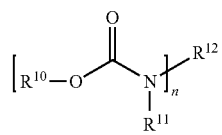

(V)

wherein
n is a number from 1 to 8 and
$R^{10}$, $R^{11}$, $R^{12}$ independently of one another, represent hydrogen or linear, branched, cyclic or heterocyclic organic radicals which are unsubstituted or optionally also substituted by heteroatoms.

14. The process according to claim 13, wherein at least one of the radicals $R^{10}$, $R^{11}$, $R^{12}$ is substituted by at least one fluorine atom.

15. The process according to claim 1, wherein the photopolymer formulation is applied to the substrate film by a printing process.

* * * * *